United States Patent [19]
Tomita et al.

[11] Patent Number: 5,817,669
[45] Date of Patent: Oct. 6, 1998

[54] COMPOUNDS, PROCESSES FOR THE PREPARATION THEREOF AND ANTI-TUMOR AGENTS

[75] Inventors: Kyoji Tomita, Toyonaka; Katsumi Chiba; Shigeki Kashimoto, both of Osaka; Koh-ichiro Shibamori, Nishinomiya; Yasunori Tsuzuki, Toyonaka, all of Japan

[73] Assignee: Dainippon Pharmaceutical Co., Ltd., Osaka, Japan

[21] Appl. No.: 765,232

[22] PCT Filed: Jun. 6, 1995

[86] PCT No.: PCT/JP95/01110

§ 371 Date: Dec. 13, 1996

§ 102(e) Date: Dec. 13, 1996

[87] PCT Pub. No.: WO95/34559

PCT Pub. Date: Dec. 21, 1995

[30] Foreign Application Priority Data

Jun. 14, 1994 [JP] Japan ................................. 6-156578
Jul. 28, 1994 [JP] Japan ................................. 6-197921
Nov. 15, 1994 [JP] Japan ................................. 6-306914
Dec. 28, 1994 [JP] Japan ................................. 6-339956
Mar. 13, 1995 [JP] Japan ................................. 7-081705

[51] Int. Cl.$^6$ ......................... A61K 31/47; C07D 401/14
[52] U.S. Cl. ......................... 514/300; 546/123; 544/279; 514/249
[58] Field of Search ......................... 546/123; 544/279; 514/300

[56] References Cited

U.S. PATENT DOCUMENTS

| | | | |
|---|---|---|---|
| 4,730,000 | 3/1988 | Chu | 514/254 |
| 5,059,597 | 10/1991 | Petersen et al. | 514/224.5 |

FOREIGN PATENT DOCUMENTS

| | | |
|---|---|---|
| 0 153 580 | 9/1985 | European Pat. Off. . |
| 0 154 780 | 9/1985 | European Pat. Off. . |
| 61-152682 | 7/1986 | Japan . |
| 61-251667 | 11/1986 | Japan . |
| 62-33176 | 2/1987 | Japan . |
| 2-85255 | 3/1990 | Japan . |
| WO86/0735 | 12/1986 | WIPO . |

OTHER PUBLICATIONS

Yamashita et al., Cancer Research, vol. 32, pp. 2818–2822, May 15, 1992.

*Primary Examiner*—Matthew V. Grumbling
*Attorney, Agent, or Firm*—Wenderoth, Lind & Ponack

[57] ABSTRACT

This invention relates to pyridone-carboxylic acid derivatives of the following formula or salts thereof:

wherein
$R_1$ is a hydrogen atom, a halogen atom, etc.,
$R_2$ is a carboxyl group etc.,
$R_3$ is a hydrogen atom etc.,
A is a nitrogen atom or CH,
m is 1 or 2, and
Y is an eliminable group or a group having the following formula:

wherein
$R_4$ is a hydrogen atom or a lower alkyl group,
Z is a hydrogen atom, a lower alkyl group, etc.,
$R_5$ is a hydrogen atom, a lower alkyl group, etc.,
n is 0 or 1, and
p is 1, 2, 3 or 4
and to processes for the preparation of these compounds, and further to anti-tumor agents which contain the above compounds as effective ingredients.

21 Claims, 12 Drawing Sheets

Fig.1 Antitumor effect against human nasopharynx cancer (KB)
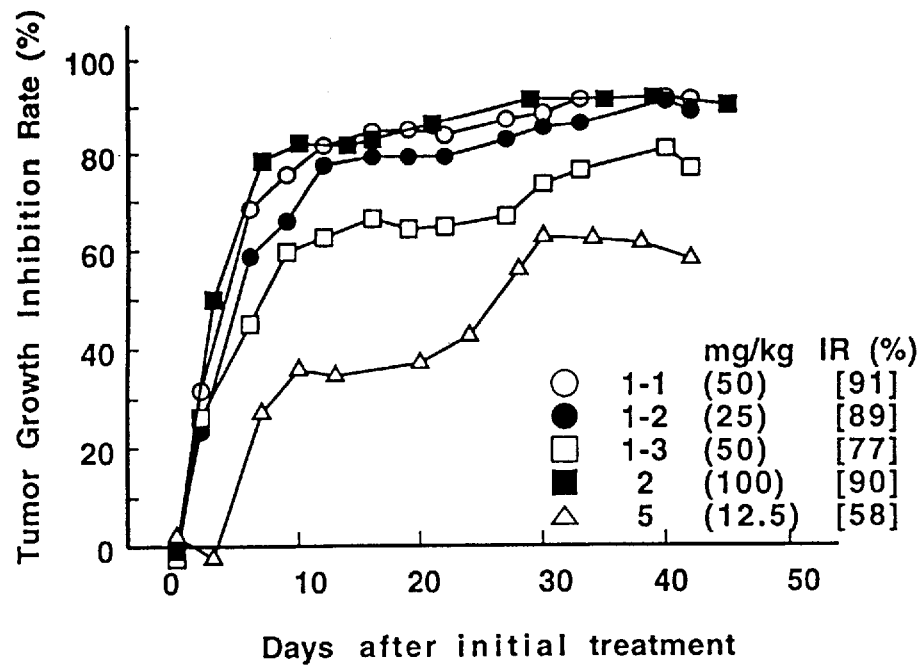
Fig.2 Antitumor effect against human nasopharynx cancer (KB)
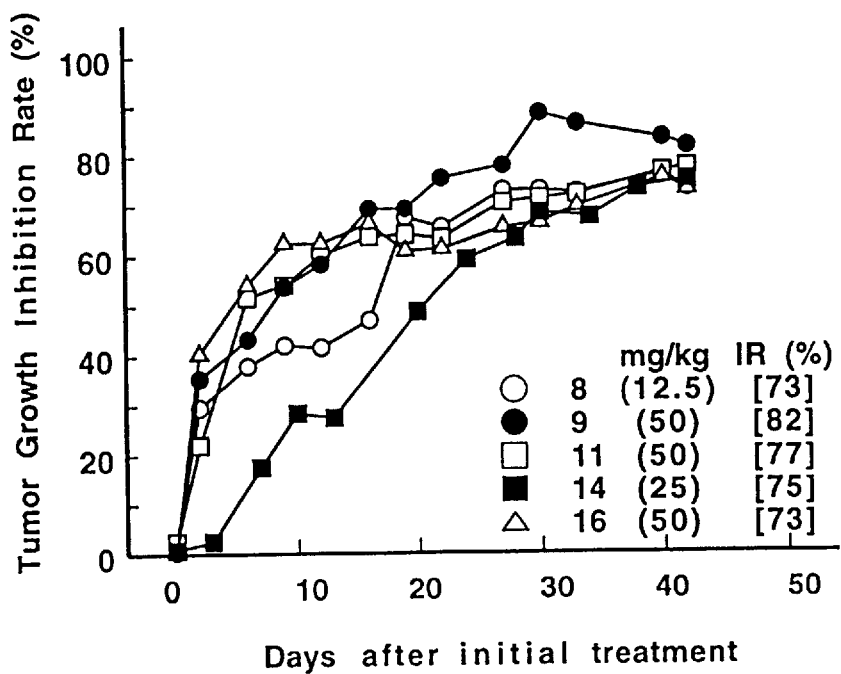

Fig.3 Antitumor effect against human breast cancer (MX-1)
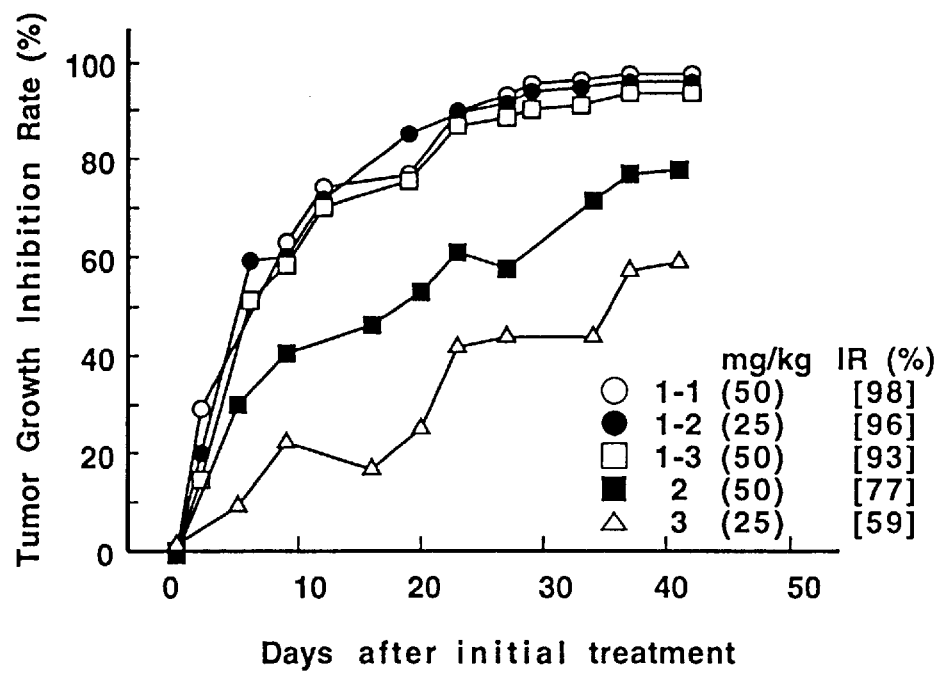
Fig.4 Antitumor effect against human breast cancer (MX-1)
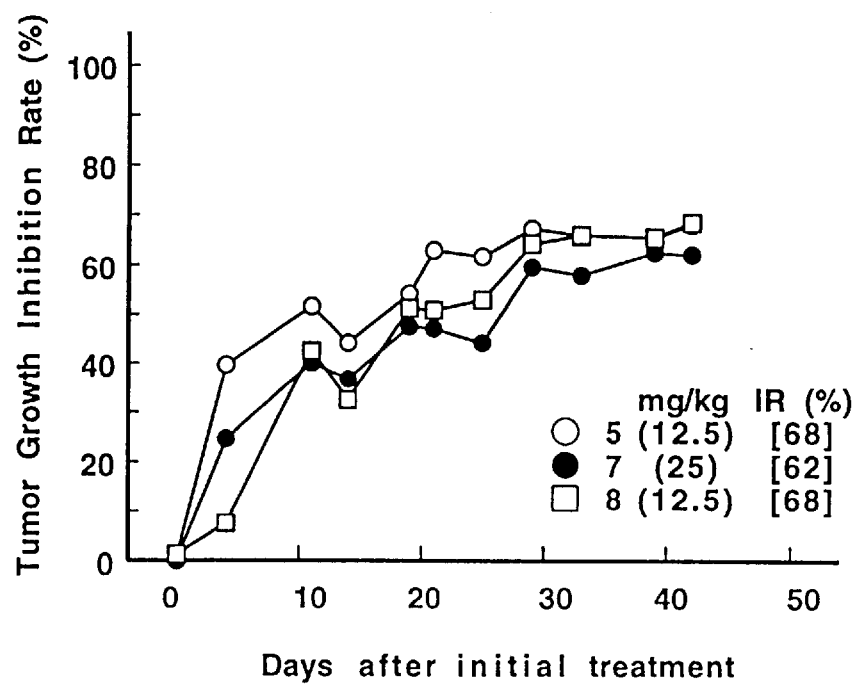

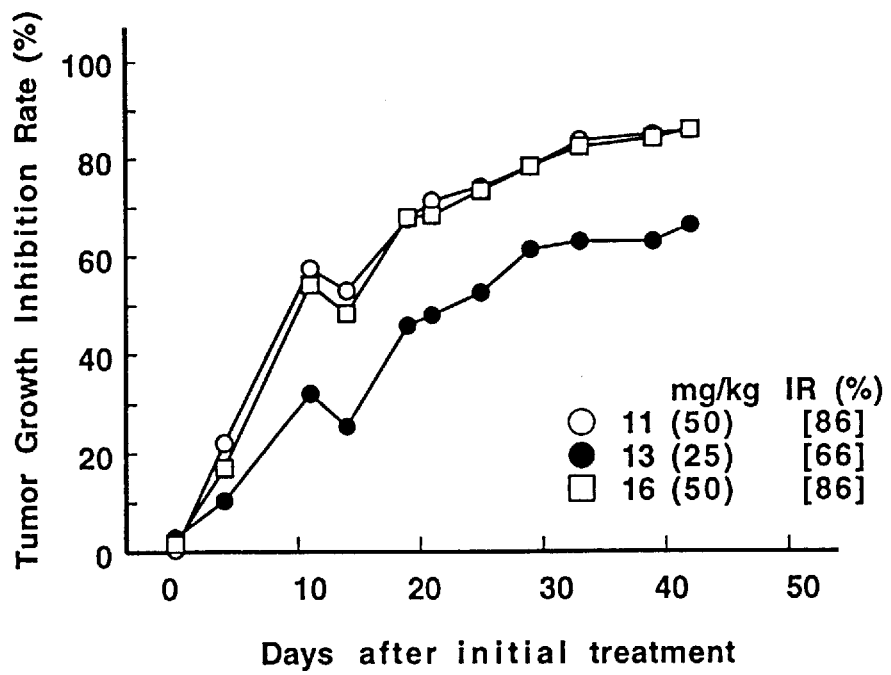
Fig.5 Antitumor effect against human breast cancer (MX-1)
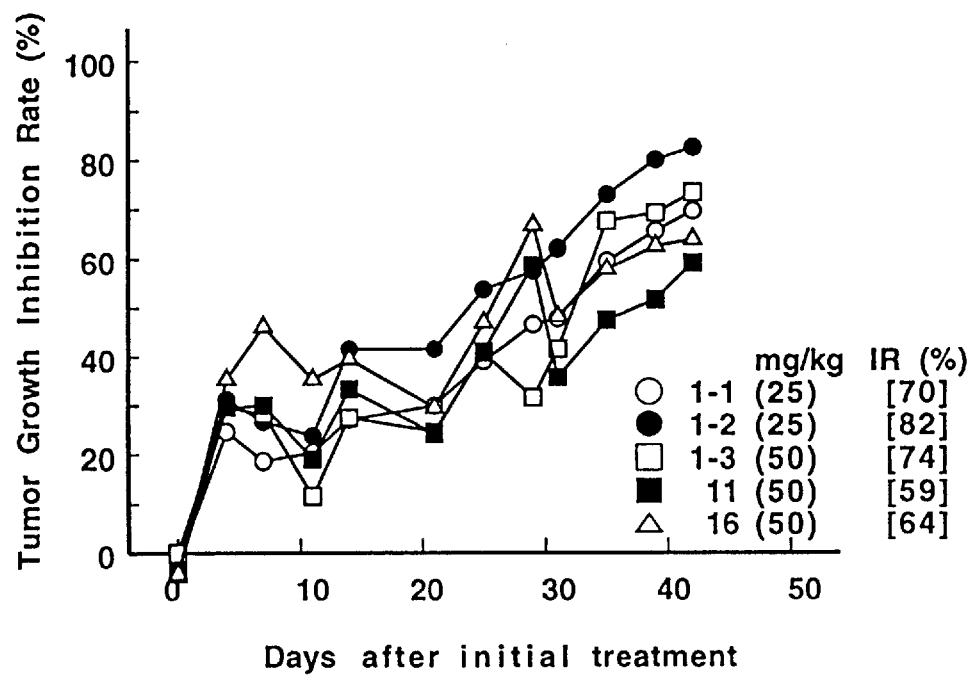
Fig.6 Antitumor effect against human colorectal cancer (WiDr)

Fig.7 Antitumor effect against human melanoma (HMV-2)
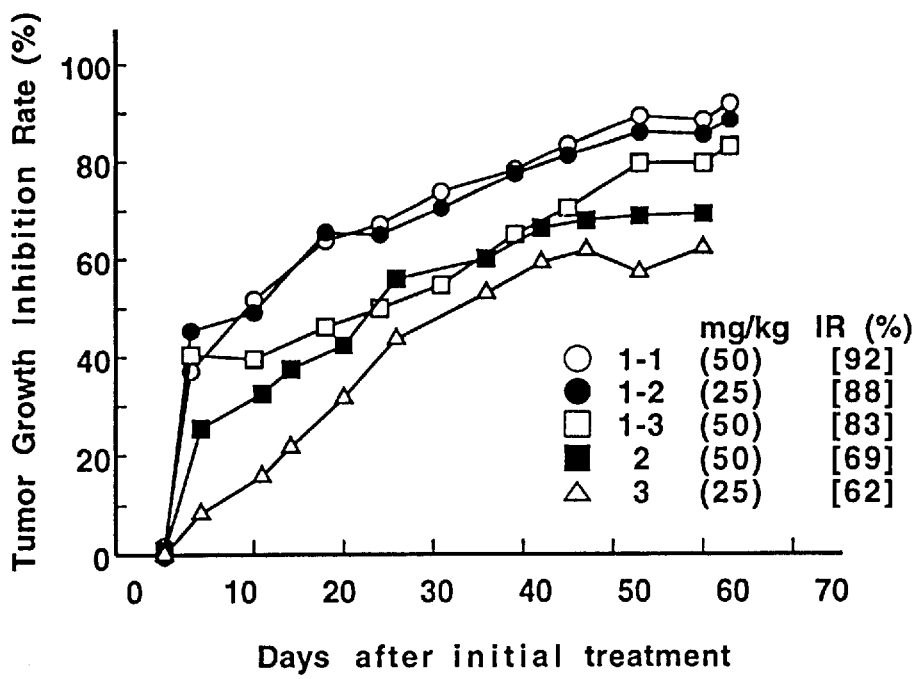
Fig.8 Antitumor effect against human melanoma (HMV-2)
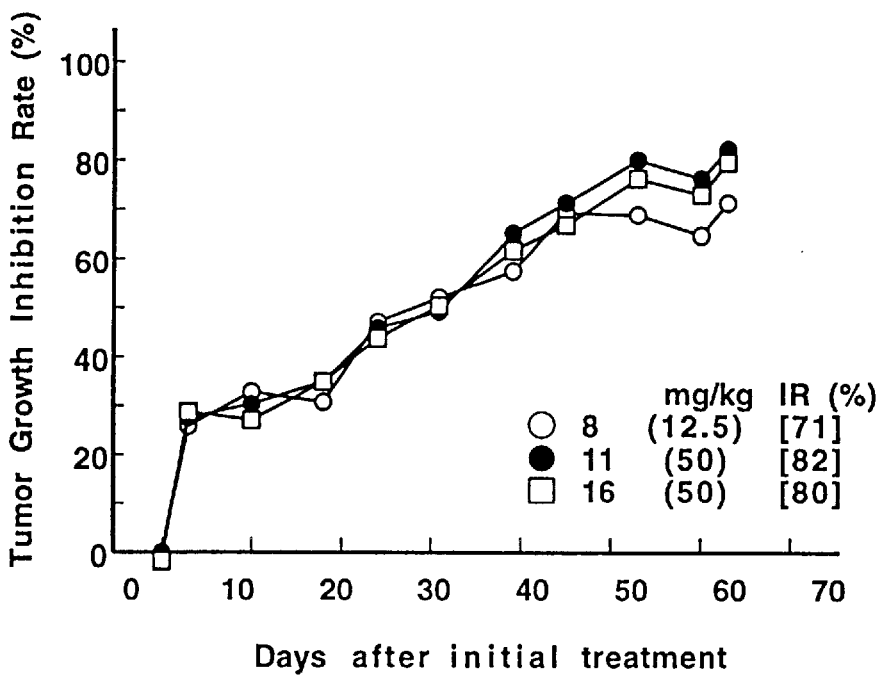

Fig.9 Antitumor effect against human lung cancer (LX-1)
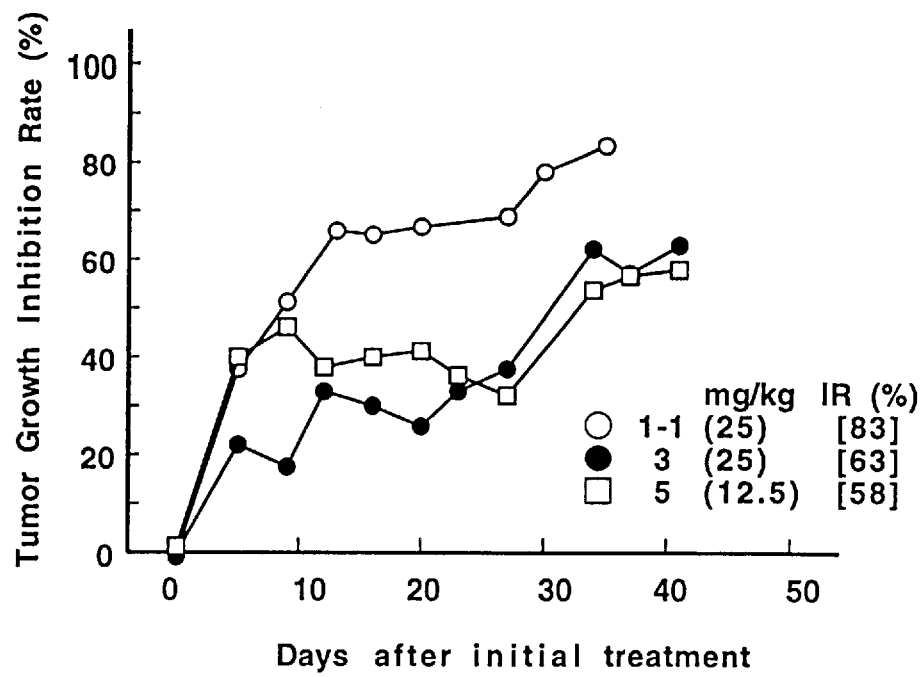
Fig.10 Antitumor effect against human nasopharynx cancer (KB)
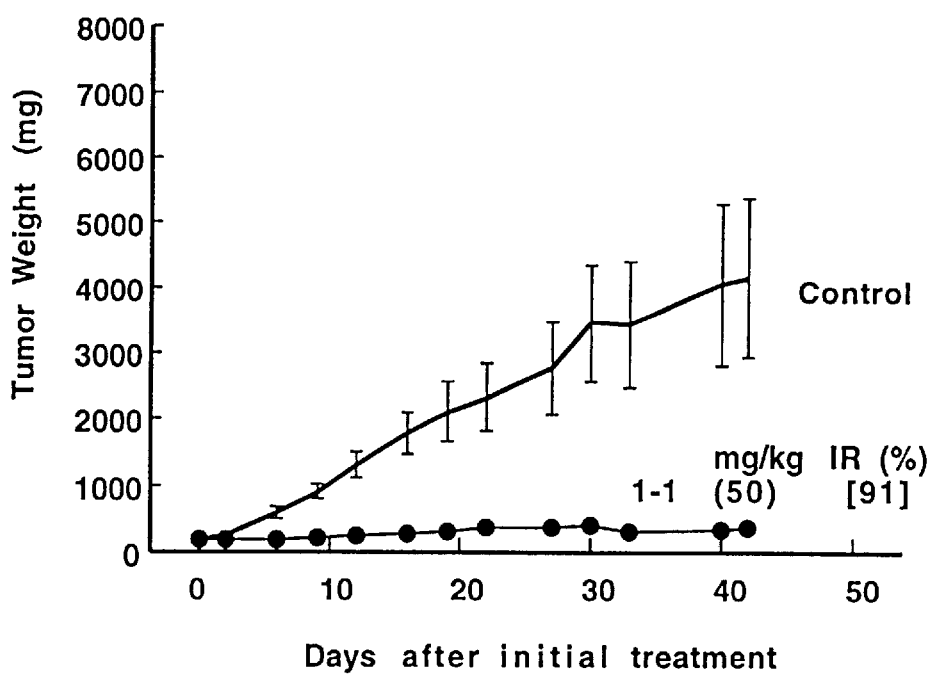

Fig.11 Antitumor effect against human breast cancer (MX-1)
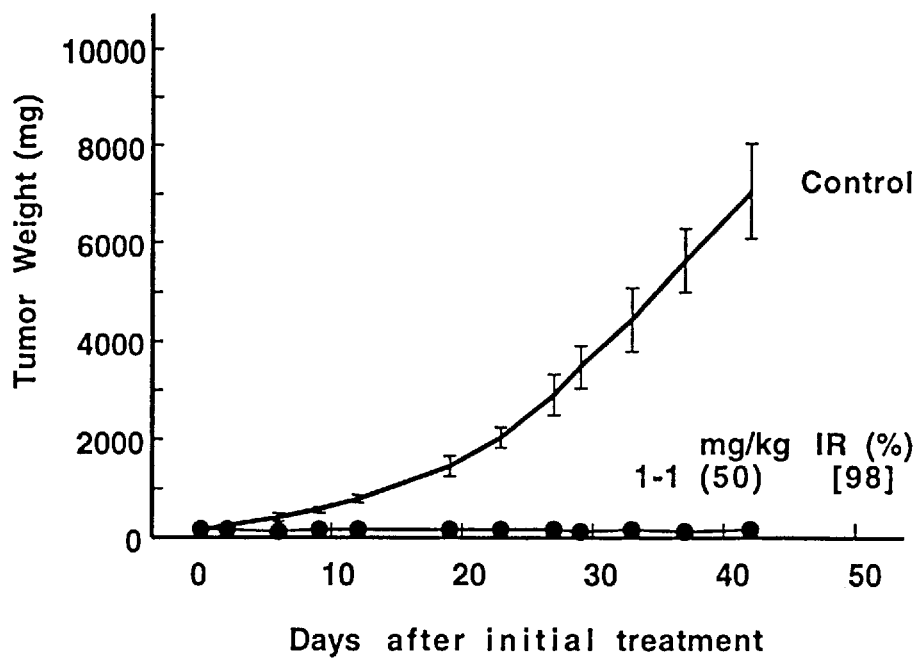
Fig.12 Antitumor effect against human colorectal cancer (WiDr)
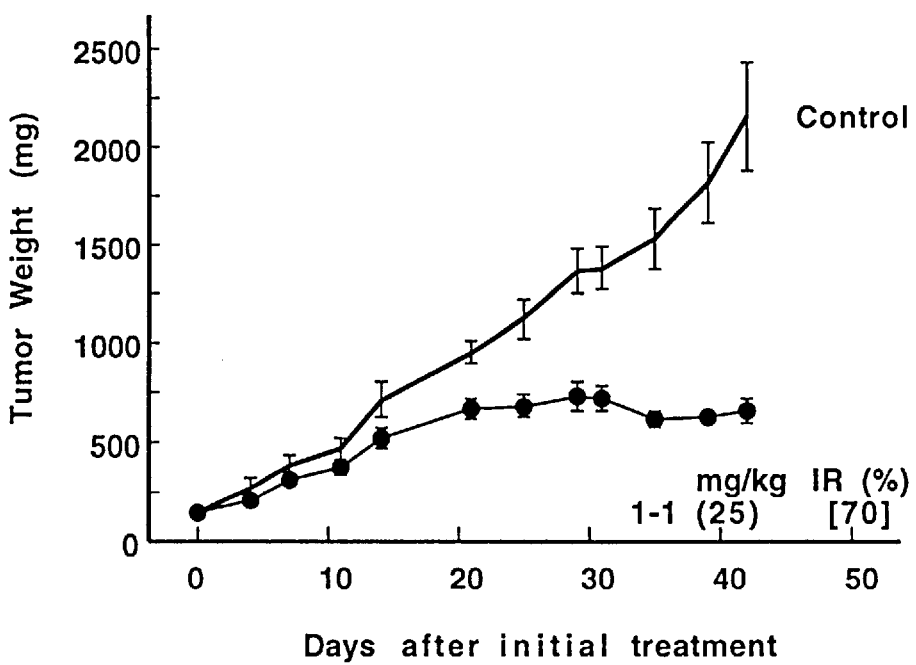

Fig.13 Antitumor effect against human melanoma (HMV-2)
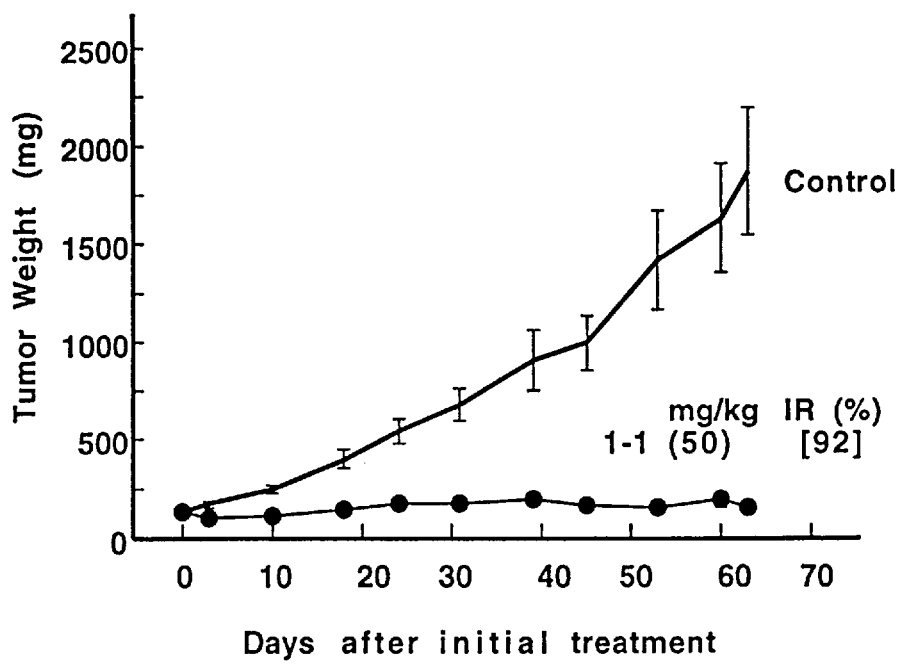
Fig.14 Antitumor effect against human lung cancer (LX-1)
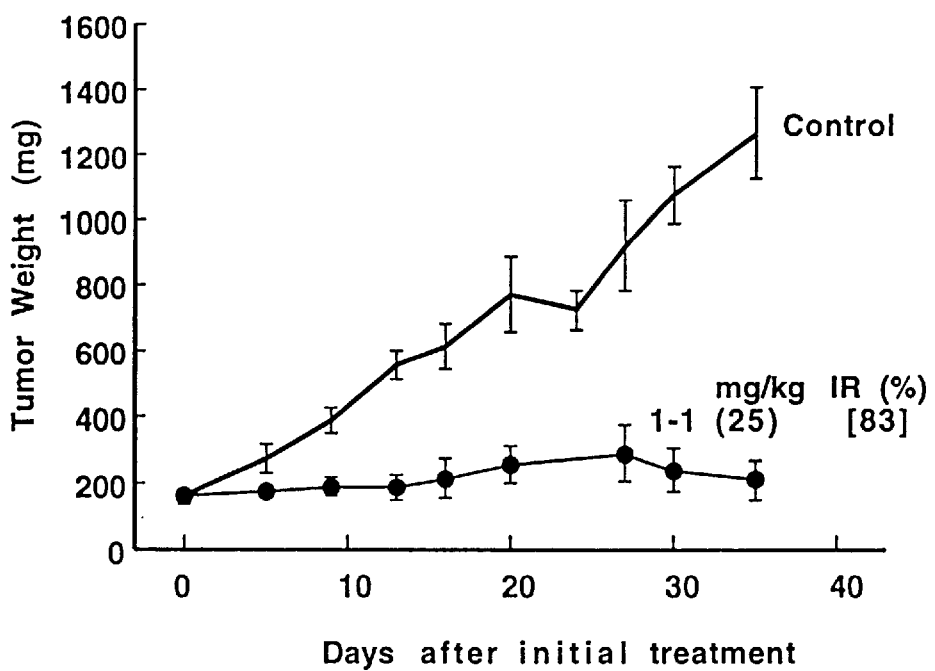

Fig. 15
Example A-1
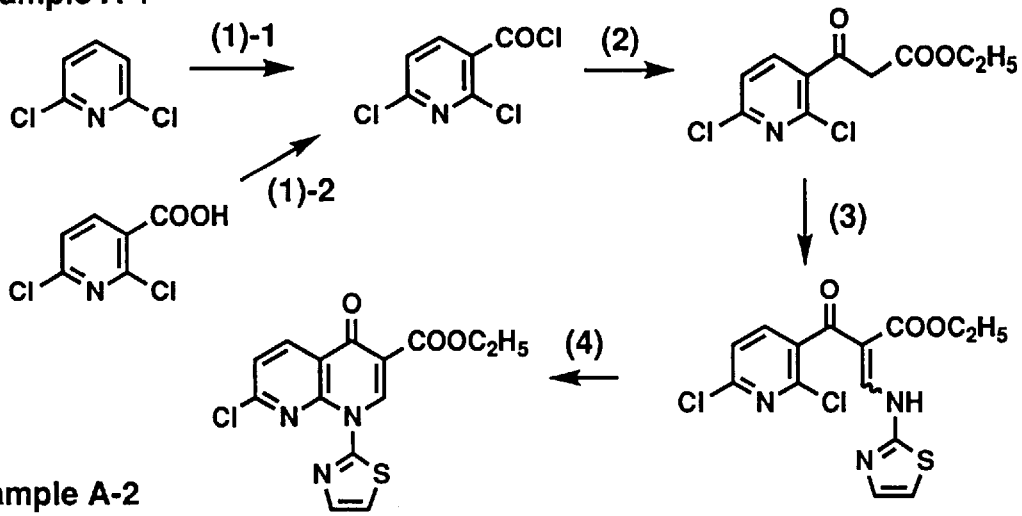
Example A-2
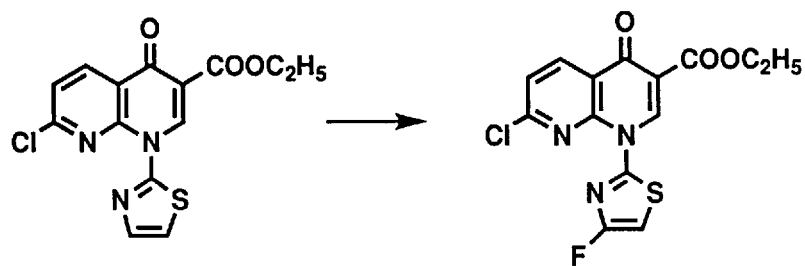
Example A-3
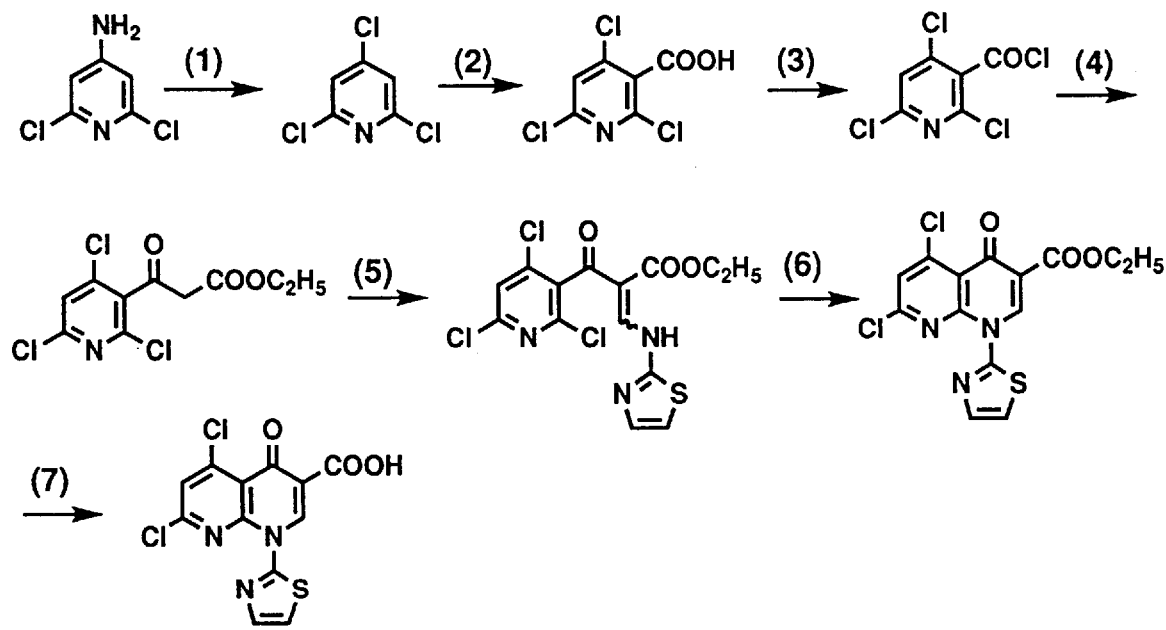

Fig. 16
Example A-4
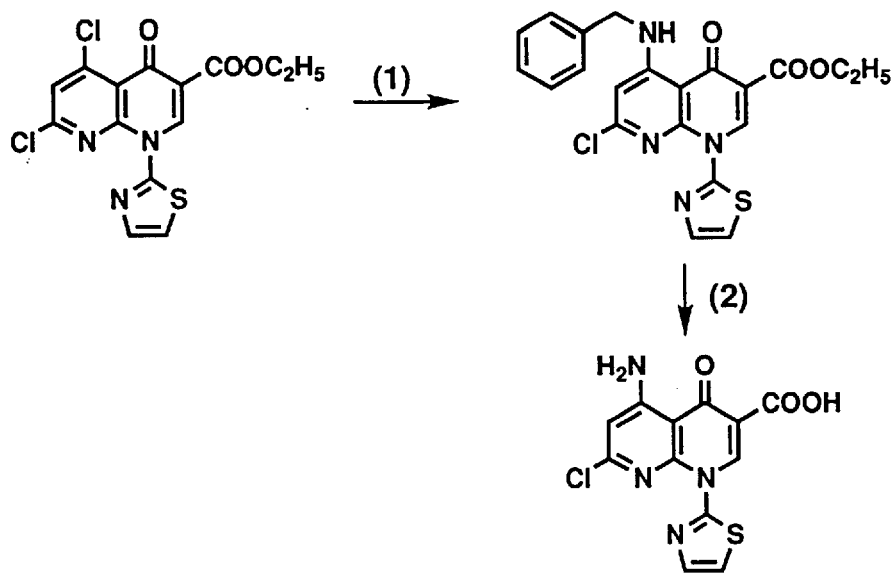
Example A-5
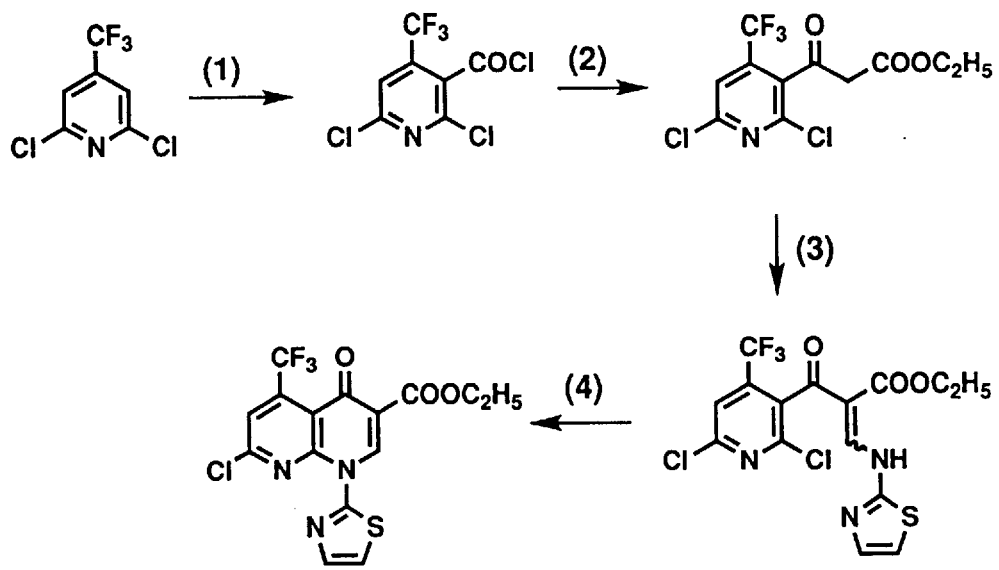

Fig. 17
Example A-6
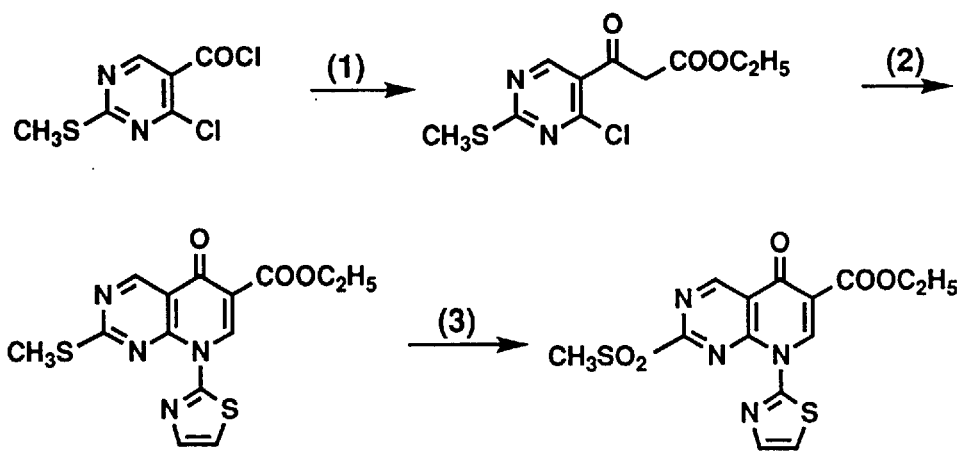
Example B-1
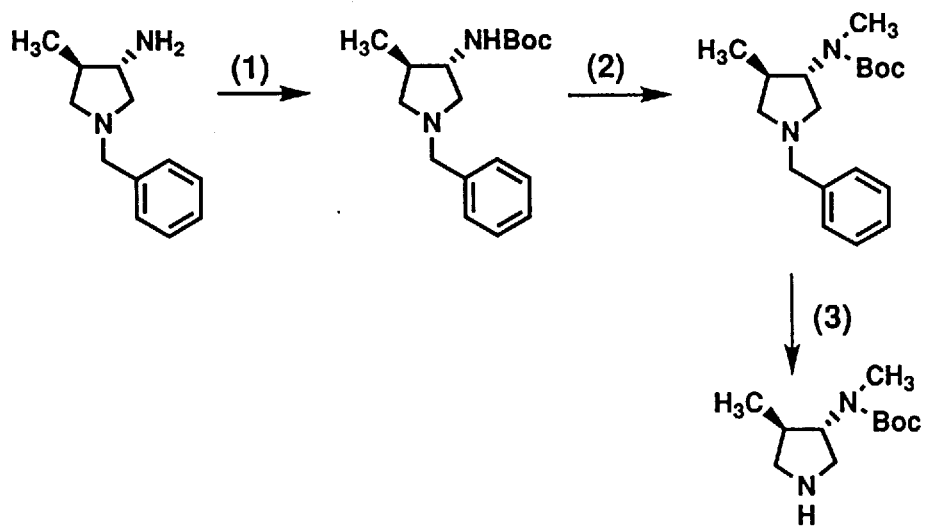

Fig. 19
Example B-4
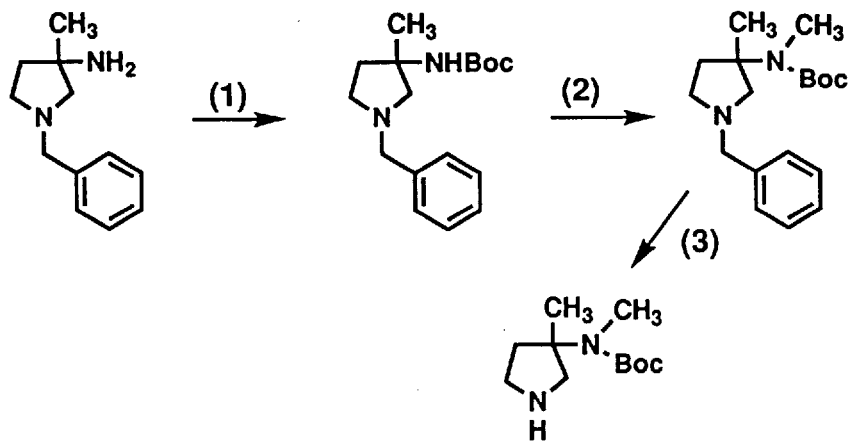
Example C-14
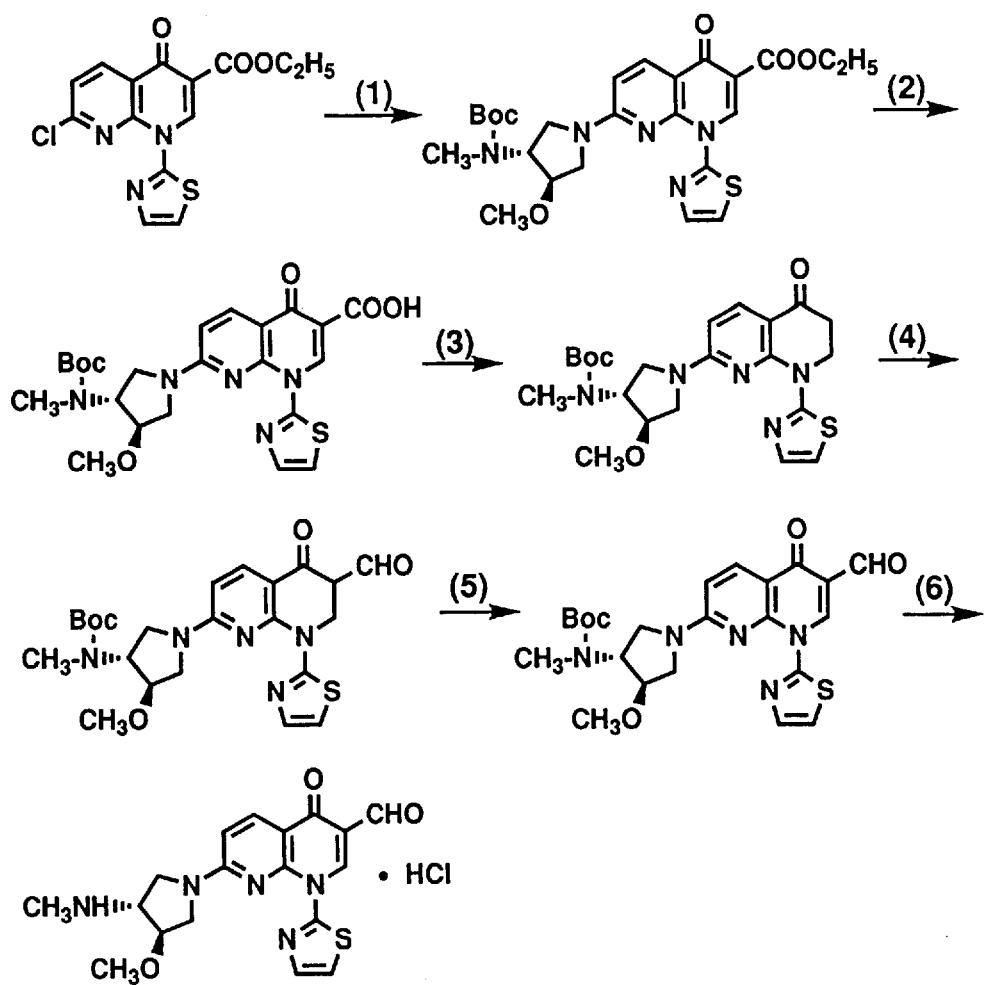

COMPOUNDS, PROCESSES FOR THE PREPARATION THEREOF AND ANTI-TUMOR AGENTS

This application claims priority under 35 U.S.C. § 371 from PCT/JP95/01110, filed Jun. 6, 1995.

TECHNICAL FIELD

This invention relates to novel pyridone-carboxylic acid derivatives, anti-tumor agents containing the same as effective ingredients, and processes for the preparation of the novel pyridone-carboxylic acid derivatives, etc.

BACKGROUND ART

There have been known both various pyridone-carboxylic acid derivatives per se which have 2-thiazolyl groups and the fact that these pyridone-carboxylic acid derivatives show anti-bacterial activity. For example, the following Compound A is disclosed in Example 24 of Japanese Patent Application Laid-Open (Kokai) No. 152682/1986 (hereinafter referred to as Ref. 1):

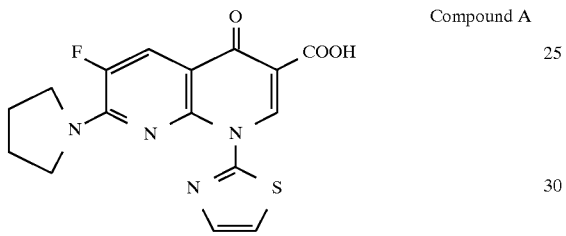

Compound A

In Example 5 of said Ref. 1, the following Compound B is exhibited:

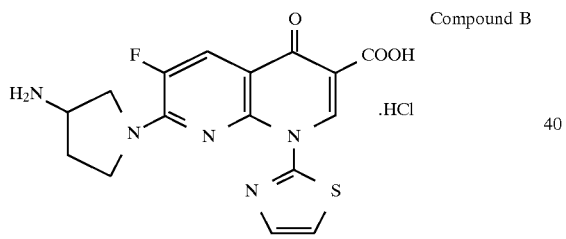

Compound B

Further, in Example 12 of Ref. 1, the following Compound C is disclosed:

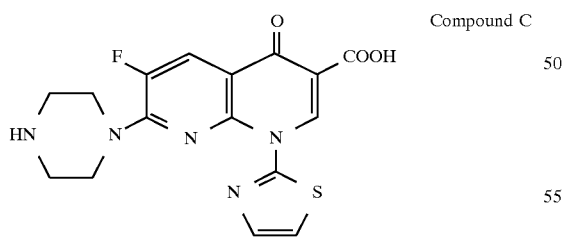

Compound C

The above compounds B and C are also disclosed in Table 1 of Japanese Patent Application Laid-Open (Kokai) No. 33176/1987 (hereinafter referred to as Ref. 2).

Moreover, the following Compound D is mentioned in Example 24-4 of Japanese Patent Application Laid-Open (Kokai) No. 56959/1985 (corresponding to European Patent Application Laid-Open No. 131839 and U.S. Pat. No. 4,730,000; hereinafter referred to as Ref. 3 together) and in Example 15 of Japanese Patent Application Laid-Open (Kokai) No. 251667/1986 (hereinafter referred to as Ref. 4).

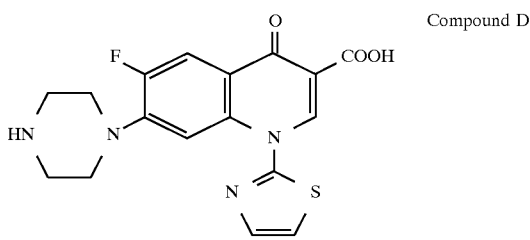

Compound D

The following Compound E is mentioned in Example 28-16 of Japanese Patent Application Laid-Open (Kokai) No. 163866/1985 (corresponding to European Patent Application Laid-Open No. 154780 and U.S. Pat. No. 4,774,246; hereinafter referred to as Ref. 5 together).

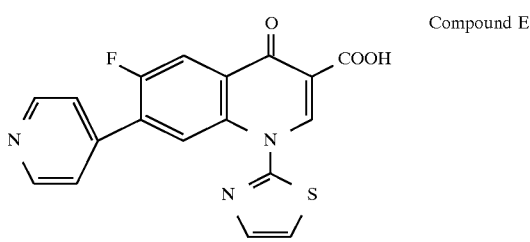

Compound E

Further, the following Compound F is shown in Example 8 of Japanese Patent Application Laid-Open (Kokai) No. 85255/1990 (hereinafter referred to as Ref. 6).

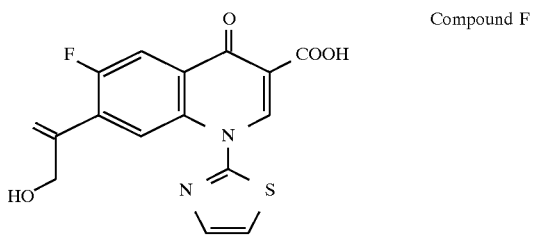

Compound F

However, the chemical structure of these compounds is different from the structure of Compound (I) of this invention in the following points (1) and (2).

(1) The 6-position of Compounds A to F is always substituted with a fluorine atom.
(2) The substituent at the 7-position of Compounds A, C, D, E and F is not a substituted 1-pyrrolidinyl group.

In addition, Refs. 1 to 6 only mention that these Compounds A to F exhibit antibacterial activity, and teach nothing on their anti-tumor activity or anti-cancer activity.

It is known that certain kinds of pyridone-carboxylic acid derivatives show anti-tumor activity or anti-cancer activity. For example, Cancer Research 52, 2818 (1992) reports that the following Compound G has anti-tumor activity:

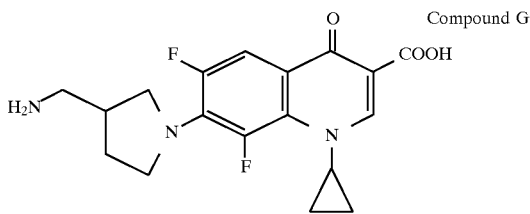

Compound G

It is reported in this treatise that 90 kinds of pyridone-carboxylic acid derivatives were investigated for anti-tumor activity, and that most of said derivatives showed no anti-tumor activity with the exception of only several types of the derivatives. It is further taught that the cyclopropyl group which is substituted at the 1-position and the two halogen atoms which are each substituted at the 6- and 8-positions play an important role for the expression of anti-tumor activity, and that a pyridone-carboxylic acid derivative which is free from such substituents shows no anti-tumor activity.

BRIEF DESCRIPTION OF DRAWINGS

FIGS. 1 to 9 show the change of tumor growth inhibition rate (IR) with the lapse of days in the case where a compound of this invention was administered to nude mice into which various human cancer cells had been transplanted.

FIGS. 10 to 14 show the change of tumor weight with the lapse of days in the above experiment.

Figure 18:
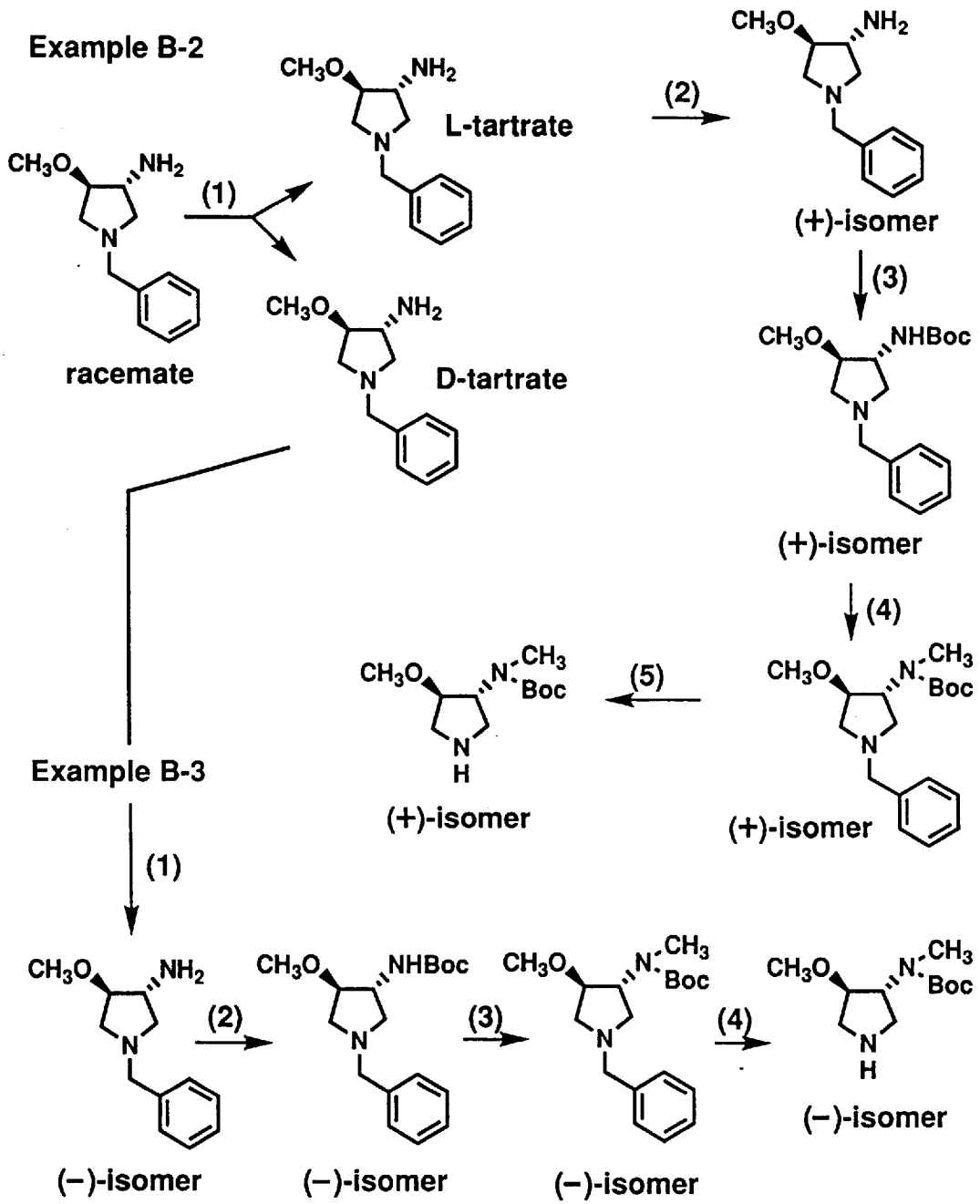

Such numerals in each Figure as "1—1 (50) [91]" each mean in this order "Compound Number, (Administered Amount mg/kg), [Tumor Growth Inhibition Rate IR % on the last day of observation].

FIGS. 15 to 19 show reaction formulae of the reactions which are mentioned in Example of Series A [Production of Intermediates of this Invention], Example of Series B [Production of Raw Materials of this Invention] and Example of Series C [Production of Compounds of this Invention] which will be mentioned later.

DISCLOSURE OF INVENTION

Seeking intensively for compounds having anti-tumor activity, the present inventors have resultantly found that novel pyridone-carboxylic acid derivatives having such 2-thiazolyl groups as may be substituted show remarkable anti-tumor activity.

This invention relates to pyridone-carboxylic acid derivatives which have 2-thiazolyl groups and which have the following general formula (I). and to salts thereof:

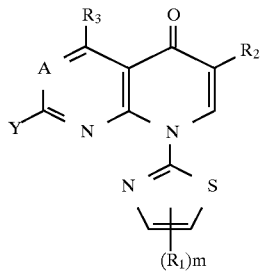

(I)

wherein $R_1$ is a hydrogen atom, a lower alkoxy group, a halogen atom, a lower alkyl group which may be substituted with halogen atom, or a phenyl group which may be substituted with halogen atom;

$R_2$ is a carboxyl group or a group convertible to a carboxyl group;

$R_3$ is a hydrogen atom, an amino group which may be protected, a halogen atom or a lower alkyl group which may be substituted with halogen atom;

A is nitrogen atom or CH;

m is an integer of 1 or 2; and

Y is an eliminable group or a group having the following formula Y'

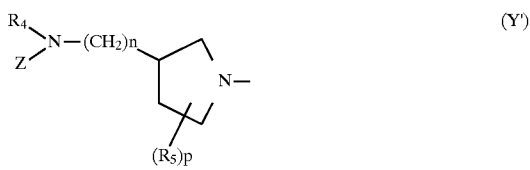

(Y')

wherein $R_4$ is a hydrogen atom or a lower alkyl group;

Z is a hydrogen atom, a lower alkyl group or a group convertible to a hydrogen atom;

$R_5$ is a hydrogen atom, a halogen atom, a lower alkoxy group, a lower alkylthio group or a lower alkyl group which may be substituted with halogen atom;

n is an integer of 0 or 1; and p is an integer of 1, 2, 3 or 4.

The compounds of this invention include, of course, their stereoisomers, optical isomers, hydrates, solvates, etc.

The compounds (I) of this invention are classified into two categories according to the character of the substituents.

One of the categories includes compounds of formula (I) wherein Y is an "eliminable group", and these compounds are useful as direct intermediates for compounds wherein Y is the above Y'. Thus, one of the objects of this invention lies in providing intermediates for pyridone-carboxylic acid derivatives which are useful as anti-tumor agents.

As the "eliminable group" included in the definition of substituent Y, any group can be used so long as it can be substituted with the later-described pyrrolidine derivative (III) and thereby eliminated, and examples of such a group include a halogen atom, a lower alkoxy group, a lower alkylthio group, a lower alkylsulfinyl group, a lower alkylsulfonyl group, an arylsulfonyl group, a lower alkylsulfonyloxy group, an arylsulfonyloxy group, etc. Among these groups, halogen atoms such as fluorine atom and chlorine atom are preferred. As for other substituents or salts, concrete examples thereof will be seen in the explanation of Compound (I-a) of this invention below.

The compounds of this invention in another category are compounds of the above formula (I) wherein substituent Y is Y', and they are useful as excellent anti-tumor agents or anti-cancer agents. Thus, this invention provides pyridone-carboxylic acid derivatives having the following formula (I-a), physiologically acceptable salts thereof, methods to produce such derivatives and salts, and anti-tumor agents which contain said derivatives or salts as effective ingredients:

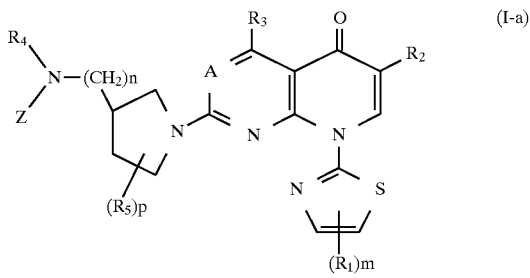

(I-a)

wherein A, $R_1$, $R_2$, $R_3$, $R_4$, $R_5$, Z, m, n and p are as defined above.

Salts of the compounds having formula (I-a) include both salts derived from the carboxyl group portion which is contained in the definition of $R_2$ of formula (I-a) and acid addition salts derived from the basic substituent group portion which is bound to the 3-position of the 1-pyrrolidinyl group.

Examples of said salts at the carboxyl group portion include salts with metals such as sodium, potassium, magnesium, zinc, silver, aluminum and platinum, and salts with organic bases such as dimethyl-aminoethanol, methylaminoethanol, triethanolamine and guanidine.

As for examples of acid addition salts at the basic substituent group which is bound to the 3-position of the 1-pyrrolidinyl group of formula (I-a), there can be taken salts with inorganic acids such as hydrochloric acid, hydrobromic acid, hydroiodic acid, sulfuric acid and phosphoric acid, and salts with organic acids such as oxalic acid, maleic acid, fumaric acid, malonic acid, lactic acid, malic acid, citric acid, tartaric acid, benzoic acid, methanesulfonic acid, p-toluenesulfonic acid, ascorbic acid, glucuronic acid, 2-hydroxy-ethanesulfonic acid, lactobionic acid and glucoheptonic acid.

Each of the above substituents is explained in the following:

In this specification, "lower alkyl group" means a straight-chain alkyl group or branched one having 1 to 5 carbon atoms, and examples of such a group include methyl group, ethyl group, n-propyl group, isopropyl group, n-butyl group, t-butyl group, etc. "Lower alkoxy group" means alkoxy group having 1 to 5 carbon atoms, and preferable examples are methoxy group and ethoxy group.

Examples of "halogen atom" include chlorine atom, fluorine atom and bromine atom.

Substituent $R_1$ in formula (I-a) is located at the 4- and/or 5-position of 2-thiazolyl group, and preferable examples include hydrogen atom, halogen atom such as fluorine atom, chlorine atom and bromine atom, lower alkoxy group such as methoxy group and ethoxy group, lower alkyl group such as methyl group and ethyl group, lower alkyl group substituted with halogen atom such as trifluoromethyl group, and phenyl group which may be substituted with halogen atom such as 3,4-difluorophenyl group.

As the "group convertible to a carboxyl group" contained in the definition of substituent $R_2$, any group can be used so long as it is convertible to a carboxyl group by a chemical means or an enzymological means, and preferable examples of such a group include hydroxy-methyl group, formyl group, ester form and physiologically acceptable salts of carboxyl group.

Examples of ester forms which are convertible to carboxyl groups mainly by a chemical means include lower alkyl esters such as methyl ester and ethyl ester.

Examples of ester forms which are convertible to carboxyl group not only through a chemical means but through an enzymological means include lower alkanoyloxy lower alkyl esters such as acetoxymethyl ester, 1-acetoxyethyl ester and pivaloyloxymethyl ester; lower alkoxycarbonyloxy lower alkyl esters such as 1-ethoxycarbonyloxyethyl ester; di-lower alkylamino lower alkyl esters such as 2-dimethylaminoethyl ester; 2-(1-piperidinyl)ethyl ester; 3-butyrolactonyl ester; choline ester; phthalidyl ester; (5-methyl-2-oxo-1,3-dioxol-4-yl) methyl ester, etc.

Preferable examples of substituent $R_3$ include hydrogen atom, halogen atom such as fluorine atom and chlorine atom, amino group, amino group protected by amino-protecting group, and lower alkyl group substituted with halogen atom such as trifluoromethyl group. As said amino-protecting group, any protecting group can be employed so long as it is easily eliminated by a usual deprotecting reaction such as hydrolysis or hydrogenolysis without giving any substantial influence on other structural portions. Concretely, said protecting group is substantially the same as the "group convertible to hydrogen atom" in the definition of substituent Z which is explained later. Preferable examples of amino-protecting group include benzyl group and trityl group.

Substituent $R_4$ is hydrogen atom or lower alkyl group, and preferably employed are hydrogen atom, methyl group and ethyl group. Incidentally, the 3-position of the 1-pyrrolidinyl group to which the basic substituent group possessing $R_4$ and Z is bound is occupied by an asymmetric carbon atom, which can cause optical isomers to be existent.

Preferable examples of substituent Z include hydrogen atom, lower alkyl group such as methyl group and ethyl group, or "group convertible to a hydrogen atom". As said "group convertible to a hydrogen atom", any group can be used so long as it is convertible to a hydrogen atom by a chemical means such as hydrolysis and hydrogenolysis or by an enzymol ogical means.

Examples of Z as such a "group convertible to a hydrogen atom" include, first, hydrolyzable groups. Concrete examples of hydrolyzable groups include acyl groups, groups having an oxycarbonyl group, amino acid residues and peptide residues, and further, for example, o-nitrophenylsulfenyl, trimethylsilyl, tetrahydro-pyranyl, diphenylphosphinyl, etc. In general, Compounds (I-a) of this invention wherein Z is an amino acid residue or peptide residue as a group convertible to a hydrogen atom are superior, in solubility, to those wherein Z is neither amino acid residue nor peptide residue, and are advantageously used in the form of liquid agents such as an injection.

Examples of the above-mentioned acyl groups include formyl, acetyl, trifluoroacetyl, etc.

Further, examples of the aforementioned groups having an oxycarbonyl group include ethoxycarbonyl, t-butoxycarbonyl [$(CH_3)_3C$—OCO—], benzyloxycarbonyl, p-methoxybenzyloxycarbonyl, vinyloxycarbonyl, β-(p-toluenesulfonyl)ethoxycarbonyl, etc.

Further, examples of amino acid residues include amino acid residues per se and such amino acid residues as are protected with a protecting group which is usually employed in peptide synthesis. Examples of protecting groups for an amino group usually employed in peptide synthesis include acyl groups such as formyl and acetyl, arylmethyloxycarbonyl groups such as benzyloxycarbonyl and p-nitrobenzyloxycarbonyl, a t-butoxycarbonyl group [$(CH_3)_3$ C—OCO—], etc.

As for amino acid residues, there can be used any, e.g., an alanine residue [$CH_3CH(NH_2)CO$—] and a leucine residue [$(CH_3)_2CHCH_2CH(NH_2)CO$—]. In general, these amino acids are represented by a set of three English letters, and this principle is followed also in the present specification. Further, L-forms, D-forms or their mixtures are distinguished by the addition of symbol "L-", "D-" or "DL-" on the head of the three letters. These symbols are omitted when these isomers are referred to as a whole.

Concrete examples of amino acid residues include residues of such amino acids as Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala.

Two to five, preferably two to three of the aforesaid amino acids form the peptide residues. As examples of such peptide residues, there can be taken residues of such peptides as Ala-Ala [$CH_3CH(NH_2)CO$—$NHCH(CH_3)CO$—], Gly-Phe, Nva-Nva, Ala-Phe, Gly-Gly, Gly-Gly-Gly, Ala-Met, Met-Met, Leu-Met and Ala-Leu.

The residues of these amino acids or peptides can take stereochemical configuration of D-form, L-form or a mixture thereof, but L-form is preferred. Further, when Z is a residue of an amino acid or peptide, also such a residue may have an asymmetric carbon atom under circumstances. Examples of amino acid residues having an asymmetric carbon atom include residues of such amino acids as Ala, Leu, Phe, Trp, Nva, Val, Met, Ser, Lys, Thr and Tyr, and, as examples of peptide residues which have an asymmetric carbon atom, there can be taken such ones as have, as a constituent ingredient, these amino acid residues having an asymmetric carbon atom.

Further, the group Z "convertible to a hydrogen atom" can be a reductively eliminable hydrogenolyzable group, and examples of such a group include arylsul fonyl groups such as o-toluenesul fonyl; methyl groups substituted with phenyl or benzyloxy such as benzyl, trityl and benzyloxymethyl; arylmethoxycarbonyl groups such as benzyloxycarbonyl and o-methoxy-benzyloxycarbonyl; and halogenoethoxycarbonyl groups such as β, β, β-tri chloroethoxycarbonyl and β-iodoethoxycarbonyl, etc.

The substituent "$(R_5)_p$-" of 1-pyrrolidinyl group of formula Y' is bound to the pyrrolidine ring of said 1-pyrrolidinyl group. The mark p denotes an integer of 1 to 4. When p is 2 to 4, $R_5$ may be identical or different. $R_5$ may be bound to any position of the 1-pyrrolidinyl group, but preferably either to the position to which the basic substituent containing both $R_4$ and Z is bound (which position is hereinafter called the 3-position of 1-pyrrolidinyl group) or to the position adjacent thereto (hereinafter called the 2- and/or 4-position of 1-pyrrolidinyl group). When $R_5$ is bound to a position other than the 3-position of the 1-pyrrolidinyl group, and when $R_5$ is not a hydrogen atom, it follows that said 1-pyrrolidinyl group have at least two asymmetric carbon atoms, with the result that the Compounds (I-a) of this invention can exist as a stereoisomer (cis form or transform) and an optical isomer. Preferable examples of substituent $R_5$ include hydrogen atom, lower alkyl groups such as methyl group and ethyl group, lower alkyl groups substituted with halogen atom such as fluoromethyl group and trifluoromethyl group, lower alkoxy group such as methoxy group and ethoxy group, lower alkylthio groups such as methylthio group, and halogen atom such as chlorine atom and fluorine atom.

The compounds (I-a) of this invention having such substituents as have been detailedly described in the above and their physiologically acceptable salts are novel and excellent in anti-tumor activity.

In the compounds of this invention having the general formula (I-a), core compounds which show anti-tumor activity have the following formula (I-b)

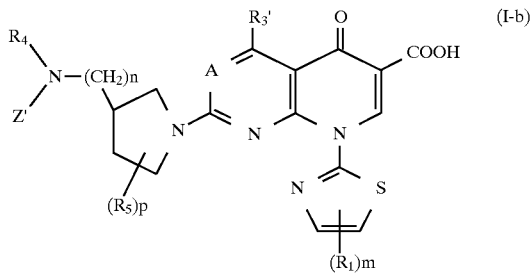

wherein $R_1$, m, $R_4$, n, $R_5$, p and A are as defined in formula (I-a); $R_3'$ is a hydrogen atom, amino group, halogen atom or lower alkyl group which may be substituted with halogen atom; and Z' is a hydrogen atom or lower alkyl group.

In the following, compounds represented by the above formula (I-b) will sometimes be abbreviated as "active compounds". When a compound which is not an active compound is administered into a living body, said compound is converted to an active compound in the living body under circumstances. In such a case, the compound which is not an active compound is sometimes abbreviated as a "prodrug". In this invention, examples of such a prodrug include compounds of formula (I-a) wherein Z is an amino acid residue or a peptide residue, or wherein $R_2$ is a formyl group or an ester form such as acetoxymethoxycarbonyl.

Further, in the description of the present specification and claims, compounds which are convertible to active compounds by any means such as a chemical means or an enzymological means are generally referred to as "convertible compounds".

The structural characteristics of the compounds (I-a) of this invention lie in that said compounds have the following constitution:

(1) the compounds have, as a basic skeleton, a pyridone carboxylic acid represented by the following formula ①

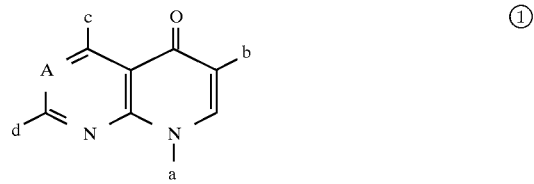

wherein A is as defined above, and a, b, c and d denote positions at which substituents are bound, (2) 2-thiazolyl group which may have a substituent is bound to the position "a", (3) a carboxyl group or a group convertible to a carboxyl group is bound to the position "b", (4) the position "c" is unsubstituted, or a group such as amino group is bound to said position, (5) A is either nitrogen atom or carbon atom which is not substituted with halogen atom such as fluorine atom, and (6) the position "d" is substituted with a specific 1-pyrrolidinyl group which has at least a substituent represented by the following formula ②

wherein $R_4$, Z and n are as defined above.

The compounds (I-a) of this invention are novel compounds which are structurally characterized in particular by the combination of the substituents which are each bound to the positions "a" and "d" and by the fact that A contains no fluorine atom.

All of the compounds of this invention included in formula (I-a) and their physiologically acceptable salts are excellent anti-tumor agents or anti-cancer agents. In particular, compounds wherein A is CH are preferable as anti-tumor agents. Much preferable are compounds wherein A is CH, m and p are 1 and n is 0.

Especially preferable are compounds wherein A is CH, m and p are 1, n is 0, $R_1$ is a hydrogen atom, $R_2$ is a carboxyl group, $R_3$ is a hydrogen atom, $R_4$ is a hydrogen atom or a lower alkyl group, Z is a hydrogen atom, and $R_5$ is a hydrogen atom, lower alkyl group or lower alkoxy group.

Examples of such compounds include 1,4-dihydro-7-(3-methoxy-4-methylamino-1-pyrrolidinyl)-4-oxo-1-(2-thiazolyl)-1,8-naphthyridine-3-carboxylic acid (see Compound 1-1 etc. in the later-described Table 1) and compounds convertible thereto.

Although concrete examples of preferable compounds included in formula (I-a) are mentioned in Examples later, the following compounds and compounds convertible thereto can be further taken as preferable examples of 1,8-naphthyridine type compounds of formula (I-a) of this invention:

- 7-(3-amino-4-fluoro-1-pyrrolidinyl)- 1,4-dihydro-4-oxo-1-(2-thiazolyl)-1,8-naphthyridine-3-carboxylic acid
- 7-(3-amino-4-methoxy-3-methyl-1-pyrrolidinyl)-1,4-dihydro-4-oxo-1-(2-thiazolyl)-1,8-naphthyridine-3-carboxylic acid
- 7-(3-amino-4-methoxy-4-methyl-1-pyrrolidinyl)-1,4-dihydro-4-oxo-1-(2-thiazolyl)-1,8-naphthyridine-3-carboxylic acid
- 7-(3-amino-3-fluoromethyl-1-pyrrolidinyl)-1,4-dihydro-4-oxo-1-(2-thiazolyl)-1,8-naphthyridine-3-carboxylic acid
- 7-(3-amino-4-fluoromethyl-1-pyrrolidinyl)-1,4-dihydro-4-oxo-1-(2-thiazolyl)-1,8-naphthyridine-3-carboxylic acid
- 7-(3-amino-4-trifluoromethyl-1-pyrrolidinyl)-1,4-dihydro-4-oxo-1-(2-thiazolyl)-1,8-naphthyridine-3-carboxylic acid
- 7-(3-amino-1-pyrrolidinyl)-1-(4-chloro-2-thiazolyl)-1,4-dihydro-4-oxo-1,8-naphthyridine-3-carboxylic acid
- 7-(3-amino-1-pyrrolidinyl)-1-(4,5-difluoro-2-thiazolyl)-1,4-dihydro-4-oxo-1,8-naphthyridine-3-carboxylic acid
- 5-amino-7-(3-amino-1-pyrrolidinyl)-1-(4-fluoro-2-thiazolyl)-1,4-dihydro-4-oxo-1,8-naphthyridine-3-carboxylic acid
- 7-(3-amino-1-pyrrolidinyl)-1-4-dihydro-4-oxo-1-(4-trifluoromethyl-2-thiazolyl)-1,8-naphthyridine-3-carboxylic acid
- 7-(3-amino-1-pyrrolidinyl)-1-[4-(3,4-difluorophenyl)-2-thiazolyl]-1,4-dihydro-4-oxo-1,8-naphthyridine-3-carboxylic acid
- 7-(3-amino-1-pyrrolidinyl)-1-(5-bromo-2-thiazolyl)-1,4-dihydro-4-oxo-1,8-naphthyridine-3-carboxylic acid The following compounds and compounds convertible thereto can be taken as examples of pyridopyrimidine type compounds of formula (I-a) of this invention:

- 5,8-dihydro-2-(trans-3-methoxy-4-methylamino-1-pyrrolidinyl)-5-oxo-8-(2-thiazolyl)pyrido[2,3-d]pyrimidine-6-carboxylic acid
- 8-(4-fluoro-2-thiazolyl)-5,8-dihydro-2-(trans-3-methoxy-4-methylamino-1-pyrrolidinyl)-5-oxopyrido[2,3-d]pyrimidine-6-carboxylic acid

PHARMACOLOGICAL TESTS

TEST EXAMPLES

The anti-tumor activity of Compounds (I-a) of this invention is described in the following. As controls, there were adopted both Compound A which is disclosed in Japanese Patent Application Laid-open No. 152682/1986 (Ref. 1) which is referred to in the beginning part of this specification, and Etoposide, i.e., a commercially available anti-cancer agent, which has the later-described structural formula.

Test Example 1

In vitro anti-tumor activity ($IC_{50}$:μg/ml) against murine P388 lymphocytic leukemia cells Test compounds were tested for anti-tumor activity according to MTT [3-(4,5-dimethylthiazol-2-yl)-2,5-diphenyltetrazolium bromide] method, using murine P388 lymphocytic leukemia cells.

A culture medium containing 1,000 to 2,000 murine P388 lymphocytic leukemia cells and test compound in predetermined concentration was put in an amount of 0.1 ml in each well of 96-well plates, and the cells were cultured for 72 hours under a condition of 37° C. and 5% carbon dioxide gas in air. After the culturing, MTT (5 mg/ml) solution was added in an amount of 0.02 ml in each well, and then, the cells were cultured for further 4 hours. The culture medium was centrifuged (4° C., 2,000 rpm for 20 minutes), and thus, the supernatants were removed by suction. Then, 0.1 ml of dimethyl sulfoxide was put in each well to dissolve the formed formazan, and, subsequently, another 0.1 ml of dimethyl sulfoxide was added. The absorbance (OD) of each of the obtained solutions was measured by use of Multiskan Bichromatic (main wavelength 570 nm, sub-wavelength 690 nm). On the supposition that the absorbance of the untreated cells (control) was 100%, 50% proliferation inhibitory concentration (50% Inhibitory Concentration: $IC_{50}$:μg/ml) were calculated by the least squares method. The results are shown in Table 1.

TABLE 1
In vitro anti-tumor activity (IC$_{50}$: μg/ml) against murine P388 lymphocytic leukemia cells
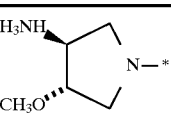
| Compound | A | R$_1$ | R$_3$ | Y' | R$_2$ | IC$_{50}$ (μg/ml) |
|---|---|---|---|---|---|---|
| 1-1 | CH | H | H | 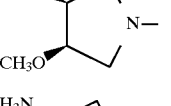 | CO$_2$H | 0.0107 |
| 1-2 | CH | H | H | Same as above [(+) form] | CO$_2$H | 0.00641 |
| 1-3 | CH | H | H | Same as above [(−) form] | CO$_2$H | 0.0200 |
| 1-4 | CH | H | H | 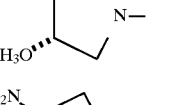 | CO$_2$H | 0.0200 |
| 2 | CH | H | H | 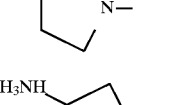 | CO$_2$H | 0.0178 |
| 3 | CH | H | H | 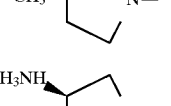 | CO$_2$H | 0.0103 |
| 4 | CH | H | H | 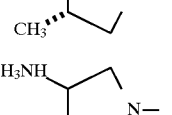 | CO$_2$H | 0.0175 |
| 5 | CH | H | H | 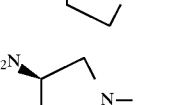 | CO$_2$H | 0.0117 |
| 6 | CH | H | H | 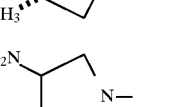 | CO$_2$H | 0.0105 |
| 7 | CH | H | H | 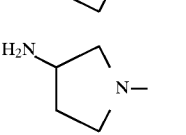 | CO$_2$H | 0.00955 |
| 8 | CH | F | H |  | CO$_2$H | 0.00413 |
| 9 | CH | H | NH$_2$ | H$_2$N<br>⟩N— | CO$_2$H | 0.00809 |

TABLE 1-continued

In vitro anti-tumor activity (IC$_{50}$: μg/ml)
against murine P388 lymphocytic leukemia cells

| Compound | A | R$_1$ | R$_3$ | Y' | R$_2$ | IC$_{50}$ (μg/ml) |
|---|---|---|---|---|---|---|
| 10 | CH | H | H | H$_2$N–C(CH$_3$)–pyrrolidinyl | CO$_2$H | 0.0192 |
| 11 | CH | H | H | CH$_3$NH–/CH$_3$O– pyrrolidinyl | CHO | 0.0309 |
| 12 | CH | H | H | H$_2$N–C(CH$_3$)(CH$_3$)–pyrrolidinyl | CO$_2$H | 0.0195 |
| 13 | CH | H | H | C$_2$H$_5$NH–/CH$_3$O– pyrrolidinyl | CO$_2$H | 0.0252 |
| 14 | N | H | H | H$_2$N–pyrrolidinyl | CO$_2$H | 0.0466 |
| 15 | CH | H | NH$_2$ | CH$_3$NH–/CH$_3$O– pyrrolidinyl | CO$_2$H | 0.0157 |
| 16 | CH | F | H | CH$_3$NH–/CH$_3$O– pyrrolidinyl | CO$_2$H | 0.0344 |
| A | CF | H | H | pyrrolidinyl | CO$_2$H | 0.0942 |
| H | | | | Etoposide | | 0.00849 |

*The steric structure of each substituent shows relative configuration (the same applies in the followings).

Compound H: Etoposide

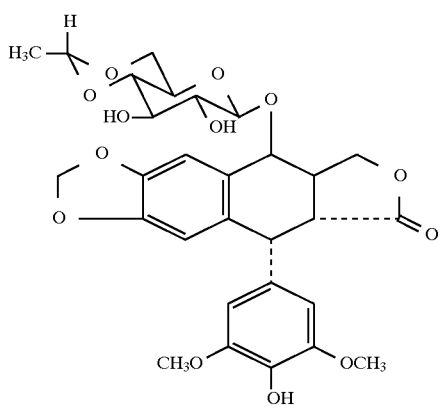

As shown in Table 1, the in vitro anti-tumor activities ($IC_{50}$) of the compounds of this invention against murine P388 lymphocytic leukemia cells are 2 to 22 times stronger than that of Compound A.

Test Example 2
In vitro anti-tumor activities against human cancer cell lines

A culture medium containing 500 to 2,000 human cancer cells was put in an amount of 0.1 ml in each well of 96-well plate, and the cells were cultured for 20 hours under a condition of 37° C. and 5% carbon dioxide gas in air. After the culturing, a solution of test compounds of predetermined concentration was added, and then, the cells were cultured for further 72 hours. After the culturing, an MTT (5 mg/ml) solution was added in an amount of 0.01 ml in the respective wells, and the cells were cultured for further 4 hours. The supernatants of the culture medium were removed by suction, and then, 0.1 ml of dimethyl sulfoxide was put in respective well to dissolve the formed formazan, and, moreover, 0.1 ml of dimethyl sulfoxide was added. With regard to the resulting solution, 50% proliferation inhibitory concentrations were calculated in the same manner as in Test example 1.

The results are shown in Table 2.

TABLE 2

In vitro anti-tumor activities ($IC_{50}$: μg/ml) against human cancer cell lines

| Com-pound | Human Cancer Cell | | | | | | |
|---|---|---|---|---|---|---|---|
| | KB | HMV-2 | AZ-521 | MKN45 | WiDr | C-33A | A-427 |
| 1-1 | 0.110 | 0.131 | 0.0561 | 0.150 | 0.379 | 0.137 | 0.0871 |
| 1-2 | 0.0873 | 0.114 | 0.0396 | 0.155 | 0.357 | 0.0828 | 0.0925 |
| 1-3 | 0.208 | 0.234 | 0.110 | 0.222 | 0.503 | 0.148 | 0.107 |
| 1-4 | 0.147 | 0.197 | 0.0985 | 0.131 | 0.273 | 0.143 | 0.158 |
| 2 | 0.309 | 0.382 | 0.331 | 0.579 | 1.88 | 0.314 | 0.169 |
| 3 | 0.153 | 0.210 | 0.181 | 0.364 | 1.08 | 0.184 | 0.0588 |
| 4 | 0.172 | 0.187 | 0.100 | 0.199 | 0.392 | 0.144 | 0.194 |
| 5 | 0.0805 | 0.0944 | 0.0433 | 0.0978 | 0.218 | 0.106 | 0.0927 |
| 6 | 0.0987 | 0.122 | 0.0622 | 0.160 | 0.381 | 0.156 | 0.0832 |
| 7 | 0.111 | 0.139 | 0.0719 | 0.112 | 0.314 | 0.105 | 0.0933 |
| 8 | 0.0494 | 0.0578 | 0.0285 | 0.143 | 0.323 | 0.0712 | 0.0625 |
| 9 | 0.106 | 0.211 | 0.0625 | 0.148 | 0.412 | 0.151 | 0.100 |
| 10 | 0.190 | 0.386 | 0.292 | 0.468 | 0.797 | 0.247 | 0.153 |
| 11 | 0.179 | 0.214 | 0.0307 | 0.144 | 0.264 | 0.161 | 0.0749 |
| 12 | 0.125 | 0.265 | 0.101 | 0.164 | 0.295 | 0.131 | 0.146 |
| 13 | 0.150 | 0.171 | 0.0717 | 0.139 | 0.268 | 0.138 | 0.150 |
| 14 | 0.636 | 0.872 | 0.310 | — | — | — | — |
| 15 | 0.0604 | 0.119 | 0.0288 | 0.0964 | 0.259 | 0.0854 | 0.0696 |
| 16 | 0.126 | 0.181 | 0.0798 | 0.148 | 0.322 | 0.132 | 0.145 |
| A | 1.94 | 2.88 | 0.797 | 1.27 | 4.09 | 0.651 | 0.854 |
| H | 0.201 | 0.298 | 0.080 | 0.490 | 1.63 | 0.084 | 0.095 |

KB: KB human nasopharynx cancer
HMV-2: HMV-2 human melanoma
AZ-521: AZ-521 human stomach cancer
MKN-45: MKN-45 human stomach cancer
WiDr: WiDr human colorectal cancer
C-33A: C-33A human cervix cancer
A-427: A-427 human lung cancer As shown in Table 2, Compounds of this invention exhibit excellent in vitro anti-tumor activities ($IC_{50}$) against human cancer cells. On the other hand, the activity of Compound A, i.e., the control, is only ½ to 1/50 as high as the compounds of this invention.

Test Example 3
Increases in life span of mice to which murine P388 lymphocytic leukemia cells had been implanted $1 \times 10^6$ murine P388 lymphocytic leukemia cells were intraperitoneally implanted in each of SLC: BDF1 mice (8 to 10 weeks old, female, 7 animals per one group). A test compound (drug) was either dissolved in 0.1 N—NaOH or suspended in 0.4% carboxymethylcellulose solution, and the resultant solution or suspension was diluted with distilled water or 0.4% carboxymethylcellulose solution so as to give predetermined concentrations for administration. The obtained solution was intraperitoneally (ip) administered twice, namely on the day following the implantation (1st day) and the 5th day, each 0.2 ml. The life and death of the mice were observed over a period of 30 days, and the median survival time (hereinafter referred to as MST) was determined for each group, and, thus, the increase in life span (ILS; %) was calculated according to the following equation:

ILS (%)=[{(MST of the test group)/(MST of the control group)}−1]×100

Drug effect was judged in the following manner, according to the criterion of U.S. National Cancer Institute (NCI):

ILS=75% or higher: ++ (remarkably effective);
20 to 74%: + (effective);
19% or lower: − (ineffective)

The results are shown in Table 3.

TABLE 3

Increases in life span of murine P388 lymphocytic leukemia cells implanted mice

| Compound | Dose (mg/kg) | ILS (%) (in solution) | ILS (%) (in suspension) | Evaluation |
|---|---|---|---|---|
| 1-1 | 50 | >275 | | ++ |
| | 25 | 200 | | ++ |
| | 12.5 | 150 | 175 | ++ |
| | 6.25 | 125 | | ++ |
| | 3.13 | 100 | 88 | ++ |
| | 1.56 | 63 | | + |
| | 0.78 | 50 | | + |
| 1-2 | 25 | >275 | | ++ |

TABLE 3-continued

Increases in life span of murine P388 lymphocytic leukemia cells implanted mice

| Compound | Dose (mg/kg) | ILS (%) (in solution) | ILS (%) (in suspension) | Evaluation |
|---|---|---|---|---|
| | 12.5 | >275 | 213 | ++ |
| | 6.25 | 175 | | ++ |
| | 3.13 | 125 | 113 | ++ |
| | 1.56 | 88 | | ++ |
| | 0.78 | 50 | | + |
| 1-3 | 50 | >275 | 200 | ++ |
| | 25 | 200 | | ++ |
| | 12.5 | 138 | 125 | ++ |
| | 6.25 | 88 | | ++ |
| | 3.13 | 63 | 63 | + |
| 1-4 | 12.5 | — | 100 | ++ |
| | 3.13 | | 25 | + |
| 2 | 50 | >275 | 238 | ++ |
| | 25 | 213 | | ++ |
| | 12.5 | 125 | 138 | ++ |
| | 6.25 | 100 | | ++ |
| | 3.13 | 88 | 63 | ++ |
| | 1.56 | 50 | | + |
| 3 | 25 | >275 | | ++ |
| | 12.5 | 188 | 175 | ++ |
| | 6.25 | 113 | | ++ |
| | 3.13 | 75 | 88 | ++ |
| | 1.56 | 63 | | + |
| 4 | 25 | 150 | | ++ |
| | 12.5 | 125 | 125 | ++ |
| | 6.25 | 88 | | ++ |
| | 3.13 | 63 | 63 | + |
| 5 | 12.5 | 188 | 188 | ++ |
| | 6.25 | 150 | | ++ |
| | 3.13 | 113 | 88 | ++ |
| | 1.56 | 50 | | + |
| 6 | 50 | | >275 | ++ |
| | 25 | 225 | | ++ |
| | 12.5 | 150 | 200 | ++ |
| | 6.25 | 138 | | ++ |
| | 3.13 | 100 | 100 | ++ |
| | 1.56 | 63 | | + |
| 7 | 50 | | 188 | ++ |
| | 12.5 | — | 100 | ++ |
| | 3.13 | | 75 | ++ |
| 8 | 12.5 | | >275 | ++ |
| | 3.13 | — | 175 | ++ |
| | 0.78 | | 75 | ++ |
| 9 | 50 | | 250 | ++ |
| | 12.5 | — | 125 | ++ |
| | 3.13 | | 100 | ++ |
| 10 | 50 | >275 | | ++ |
| | 25 | 125 | | ++ |
| | 12.5 | 100 | 113 | ++ |
| | 6.25 | 75 | | ++ |
| | 3.13 | 63 | 50 | + |
| 11 | 50 | | 225 | ++ |
| | 12.5 | — | 150 | ++ |
| | 3.13 | | 88 | ++ |
| 12 | 12.5 | — | 75 | ++ |
| 13 | 50 | | 213 | ++ |
| | 12.5 | — | 100 | ++ |
| | 3.13 | | 25 | + |
| 14 | 50 | | >275 | ++ |
| | 12.5 | — | 113 | ++ |
| | 3.13 | | 63 | + |
| 15 | 50 | | 238 | ++ |
| | 12.5 | — | 200 | ++ |
| | 3.13 | | 88 | ++ |
| 16 | 50 | | 238 | ++ |
| | 12.5 | — | 138 | ++ |
| | 3.13 | | 38 | + |
| 17 | 50 | — | 150 | ++ |
| A | 50 | 38 | | + |
| | 25 | 25 | — | + |
| | 12.5 | 0 | | — |
| H | 25 | >275 | | ++ |
| | 12.5 | 150 | | ++ |

TABLE 3-continued

Increases in life span of murine P388 lymphocytic leukemia cells implanted mice

| Compound | Dose (mg/kg) | ILS (%) (in solution) | ILS (%) (in suspension) | Evaluation |
|---|---|---|---|---|
| | 6.25 | 100 | — | ++ |
| | 3.13 | 75 | | ++ |
| | 1.56 | 50 | | + |

As shown in Table 3, the effects of the compounds of this invention on increase in life span of mice to which murine P388 lymphocytic leukemia cells were implanted are much superior to the effects of Compound A as a control.

Test Example 4

Tumor growth inhibition effect on colon 26 murine tumor cells implanted mice

A 2% brei of colon 26 murine tumor cells was intracutaneously implanted each 0.1 ml in the abdominal part of SLC: $CDF_1$ female mice (7 to 9 weeks old, 7 animals per one group). Then, test compound (drug) was dissolved in 0.1 N—NaOH, and diluted with distilled water to give predetermined concentrations for administration. The obtained solutions were intraperitoneally (ip) administered each 0.2 ml once a day, from the day (1st day) following the implantation to the 9th day. On the 21st or 22nd day after the implantation, tumor weight was estimated from tumor diameters, and thus, the tumor growth inhibition rate (IR %) of the drug administered group in comparison with the control group was calculated according to the following equation.

IR (%)=[1−{(MTW in the treated group)/(MTW in the control group)}]×100

MTW: mean tumor weight

TABLE 4

Tumor growth inhibition rate (IR) of colon 26 murine tumor cells implanted mice

| Compound | Dose (mg/kg) | IR (%) |
|---|---|---|
| 1-1 | 1.56 | 86 |
| 1-2 | 1.10 | 69 |
| 1-3 | 1.56 | 50 |
| | 2.21 | 75 |
| 1-4 | 3.13 | 61 |
| 2 | 12.5 | 79 |
| 3 | 3.13 | 77 |
| 4 | 1.56 | 64 |
| | 3.13 | 89 |
| 5 | 1.56 | 78 |
| 6 | 1.56 | 71 |
| 7 | 1.56 | 61 |
| | 3.13 | 95 |
| 8 | 0.39 | 57 |
| | 1.56 | 91 |
| 9 | 3.13 | 62 |
| | 6.25 | 97 |
| 10 | 3.13 | 74 |
| 11 | 0.78 | 50 |
| | 1.56 | 58 |
| 12 | 3.13 | 48 |
| | 6.25 | 84 |
| 13 | 1.56 | 41 |
| 14 | 3.13 | 55 |
| | 6.25 | 68 |
| 15 | 3.13 | 68 |

TABLE 4-continued

Tumor growth inhibition rate (IR) of colon 26 murine tumor cells implanted mice

| Compound | Dose (mg/kg) | IR (%) |
|---|---|---|
| 16 | 3.13 | 77 |
| A | 12.5 | 23 |
| H | 12.5 | 57 |

As shown in Table 4, the tumor growth inhibition rate (IR) of the compounds of this invention in colon 26 murine tumor cells implanted in mice are excellent. On the other hand, the effect of Compound A is apparently inferior to the compounds of this invention in view of both doses and inhibition rates.

In the following Test examples 5 to 9, human cancer cells were implanted in nude mice, to which test compounds dissolved in an aqueous solution containing NaOH were administered, and, thus, the degree of growth inhibition of cancer cells was observed.

The results of Test examples 5 to 9 are shown in FIGS. 1–14.

FIGS. 1–9 show the variation with the lapse of days of IR.

FIGS. 10–14 show the relation between tumor weight and the lapse of days in the case where Compound 1—1 was used in Test examples 5–9. Vertical axis corresponds to tumor weight, and horizontal axis corresponds to the days which passed after the start of administration. Tumor weight was estimated from tumor diameter. The term Control in FIGS. 10–14 means tumor weight variation with days in nude mice to which, although cancer cells had been implanted, no test compounds had been administered.

Each of Figures shows the amount of each compound administered (mg/kg/day) and IR (%) on the last day of observation which is explained in Test example 4.

In the following, there is explained schedule of administration of test compounds in nude mice. After days of x in number have passed from implantation of human cancer cells in nude mice, test compounds are intraperitoneally (ip) administered for y days, followed by wash-out periods of days of z in number. Thereafter, test compounds are administered again for y days. In this case, the cycle of administration (y days) and discontinuation (z days) is called "course". Such a schedule is denoted by marks as follows:

[(x) (y) (z) (course) (ip)]

These marks are explained below with an example. The mark "↑" means the day on which test compounds are administered.

Example: Test compounds are administered (ip) after 25 days from implantation, and, then, administration is suspended for six days, and, thereafter, administration is conducted again. This operation is repeated five times.

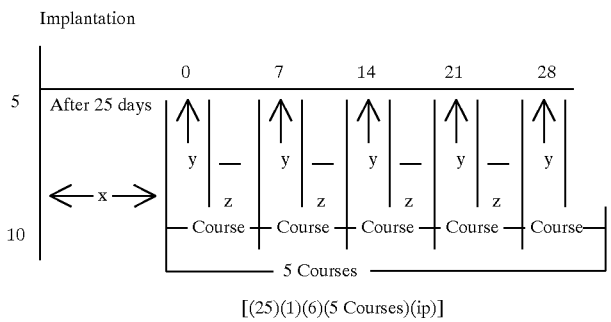

[(25)(1)(6)(5 Courses)(ip)]

Test Example 5
Anti-tumor effect on KB human nasopharynx cancer implanted in nude mice
  Experiment was conducted under the following condition:
  Condition:
    Animal used: Female BALB/cAnNCrj-nu/nu nude mice (9 and 14 weeks old, 6 animals per one group)
    Cancer cells used: Human nasopharynx cancer cell KB
    Implantation of cancer cells:
      2.5×106 cancer cells were intracutaneously implanted at the abdominal part of nude mice
    Administration schedule:
      [(5)(1)(6)(6 courses)(ip)]
    Results: Shown in FIGS. 1–2 and 10

Test Example 6
Anti-tumor effect on MX-1 human breast cancer cells implanted in nude mice
  Experiment was conducted under the following condition:
  Condition:
    Animal used: Female BALB/cAnNCrj-nu/nu nude mice (9 weeks old, 5–6 animals per one group)
    Cancer cells used: Human breast cancer MX-1
    Implantation of cancer cells:
      A piece of cancer tissue of 2 mm3 was subcutaneously implanted at the back part of nude mice
    Administration schedule:
      [(16 and 23)(1)(6)(6 courses)(ip)]
    Results: Shown in FIGS. 3–5 and 11

Test Example 7
Anti-tumor effect on WiDr human colorectal cancer cells implanted in nude mice
  Experiment was conducted under the following condition:
  Condition:
    Animal used: Female BALB/cAnNCrj-nu/nu nude mice (9 weeks old, 6 animals per one group)
    Cancer cells used: Human colorectal cancer WiDr
    Implantation of cancer cells:
      2.5×106 cancer cells were intracutaneously implanted at the abdominal part of nude mice
    Administration schedule:
      [(9)(1)(6)(6 courses)(ip)]
    Results: Shown in FIGS. 6 and 12

Test Example 8
Anti-tumor effect on HMV-2 human melanoma cells implanted in nude mice
  Experiment was conducted under the following condition:
  Condition:
    Animal used: Female BALB/cAnNCrj-nu/nu and BALB/c nu/nu nude mice (11–15 weeks old, 6–7 animals per one group)

Cancer cells used: Human melanoma HMV-2
Implantation of cancer cells:
  4.4×106 cancer cells were intracutaneously implanted at the abdominal part of nude mice
Administration schedule:
  [(8–9)(1)(6)(9 courses)(ip)]
Results: Shown in FIGS. 7–8 and 13

Test Example 9

Anti-tumor effect on LX-1 human lung cancer cells implanted in nude mice

Experiment was conducted under the following condition:

Condition:
  Animal used: Female BALB/cAnNCrj-nu/nu nude mice (13 weeks old, 6 animals per one group)
  Cancer cells used: Human lung cancer LX-1
  Implantation of cancer cells:
    A piece of cancer tissue of 2 mm3 was subcutaneously implanted at the back part of nude mice
  Administration schedule:
    [(19 and 26)(1)(6)(5–6 courses)(ip)]
  Results: Shown in FIGS. 9 and 14

As is seen in the above-mentioned FIGS. 1–14, the compounds of this invention remarkably inhibited the growth of human cancer cells implanted in nude mice.

Test Example 10

Acute toxicity

Solutions of test compounds in predetermined concentrations were administered (0.1 ml/10 g body weight) to female BALB/c CrSlc mice (5 to 10 animals per one group, 10 weeks old) respectively, and, thus, $LD_{50}$ values were calculated from the mortalities of the mice on the 14th day after the administration. The results are shown in the following table.

TABLE 5

Acute toxicity ($LD_{50}$: mg/kg)

| Compound | Intraperitoneal administration (ip) | Intravenous administration (iv) |
|---|---|---|
| 1-1 | 93.2 | — |
| 2 | 135 | — |
| 3 | 55.2 | 119 |
| 4 | — | >100 |
| 5 | — | 66.7 |
| H | 71 | 123 |

As is shown in Table 5, the acute toxicity of the compounds of this invention are almost equal to that of Compound H (Etoposide), a commercially available anti-cancer agent.

Test Example 11

Solubility

The solubilities of Compound 1-1, 1-1-3, 3 and 3-1 in 0.1M phosphate buffer (pH 7.2) and in distilled water were measured, and the following results were obtained.

Compound 1-1-3 is an L-Ala derivative of Compound 1-1 and is prepared according to Example C-1 (5), while Compound 3-1 is an L-Ala derivative of Compound 3 and is prepared according to Example C-6 (4).

TABLE 6

Solubility

| Compound | Distilled water (mg/ml) | 0.1 M phosphate buffer (pH 7.2) (mg/ml) |
|---|---|---|
| 1-1 | 2.9 | 20.1 |
| 1-1-3 | >98.7 | >233.5 |
| 3 | 8.3 | — |
| 3-1 | 79.4 | — |

As shown in Table 6, Compounds 1-1-3 and 3-1 whose Z is an amino acid residue exhibited a solubility about 10 times or higher than that of Compound 1-1 and 3 whose Z is a hydrogen atom. Besides, the solubility of Compound 1-1 in neutral state is so high that it is suitable as a liquid agent such as injection.

As shown in the above test results, the compounds of this invention exhibit remarkable anti-tumor activity against not only non-solid tumors such as lymphocytic leukemia tumor but also various solid tumors which occur in tissues of, for example, lung, breast, stomach, uterus, skin, intestine, bladder and nasopharynx. Further, the compounds of this invention have comparatively high safety. The compounds are therefore useful as agents for the treatment or prophylaxis of human tumors.

The compounds of this invention are administered in such an amount as to inhibit tumor, which amount varies depending on their pharmacodynamic characteristics, way of administration, symptoms and ages, objective of administration (prophylaxis or treatment), etc. Usually, however, the compounds are administered in an amount of about 0.25 mg to about 50 mg, preferably about 0.5 mg to about 20 mg, per one day and per kg of body weight. For example, about 13 mg to about 2.5 g, preferably 25 mg to 1 g in total of active ingredient is administered per day in a patient having a body weight of about 50 kg. The above dose of a day may be divided into two to four and administered separately. The administration route may be either oral or parenteral, but parenteral administration is recommended.

The compounds of this invention are generally administered in the form of pharmaceutical preparations. These preparations can be prepared by compounding the compounds of this invention with pharmaceutical carriers. For example, a pharmaceutical carrier for liquid agents as pharmaceutical preparations for parenteral administration contains a solvent as an essential ingredient and, if necessary, auxiliaries such as tonicity agents, solubilizers, soothing agents, pH-adjusting agents, buffers and preservatives.

As for a solvent, there are generally employed water, organic solvent such as propylene glycol or a mixture of water wi th organic solvent.

Examples of tonicity agent include sugars such as Sorbit and Mannit, and sodium chloride, but sugars are much preferable.

As for pH-adjusting agent, there can be employed bases such as sodium hydroxide and acids such as hydrochloric acid and phosphoric acid.

Examples of solubilizer include surfactants such as Polysorbate 80 and Pluronic F68, and organic acids such as lactic acid and methanesulfonic acid which can form an acid addition salt together with the compounds of this invention.

As for soothing agent, there can be employed lidocaine hydrochloride and procaine hydrochloride. As for preservative, there can be used benzylalcohol, and as examples of stabilizer, there can be taken antioxidant such as ascorbic acid. As for buffer, there can be employed salts of acid such as phosphoric acid, citric acid and lactic acid.

Liquid agents such as injections and infusions can be prepared by dissolving or suspending, preferably dissolving the compounds of this invention in a solvent, and by, if necessary, compounding other auxiliaries before or after the dissolution or suspension. Lyophilized pharmaceutical preparations can be prepared by freeze-drying these liquids. When administered, the lyophilized pharmaceutical preparations are re-dissolved or re-suspended.

As for carriers in solid pharmaceutical preparations such as tablets, capsules, granules, fine granules and powders, any can be used so long as they do not react with the compounds of this invention and so long as they are used in this art. Concrete examples of such carriers include starches, mannitol, crystalline cellulose, carboxymethylcellulose, etc.

These pharmaceutical preparations may further contain ingredients useful for medical treatment other than the compounds of this invention.

Preparation Processes

Processes for the preparation of the compounds of this invention are as follows. Compounds (I) of this invention and their salts can be prepared according to (a) pyrrolidine substitution reaction, (b) ring closing reaction, (c) oxidation reaction, etc.

(a) Pyrrolidine substitution reaction

Among the compounds of this invention of formula (I), both compound (I-a) wherein Y is 1-pyrrolidinyl group (Y') having a substituent and a salt thereof can be prepared by making a compound having the following formula (II) or a salt thereof

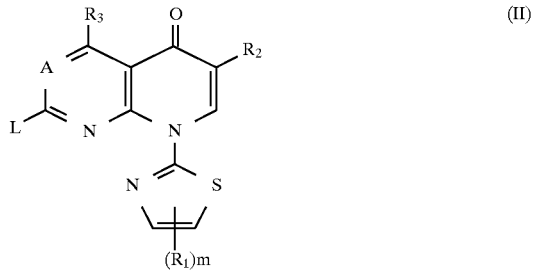

wherein L is an eliminable group, and A, $R_1$, $R_2$, $R_3$ and m are as defined above,
react with a pyrrolidine derivative of the following formula (III)

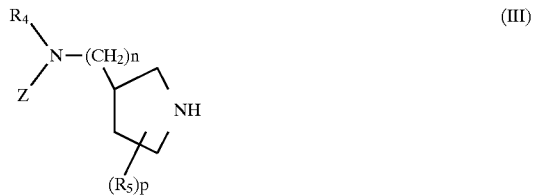

wherein $R_4$, $R_5$, Z, n and p are as defined above.

As for the eliminable group (L) in the formula (II), there can be mentioned the same groups as in the case of formula (I) where Y is an eliminable group, and preferable example of group (L) include halogen atom, lower alkoxy group, lower alkylthio group, lower alkylsulfinyl group, lower alkylsulfonyl group, arylsulfonyl group, lower alkylsulfonyloxy group, arylsulfonyloxy group, etc.

The above reaction can be conducted either without any solvent or in a suitable solvent, and preferably in the presence of a base, at a temperature ranging from 10° to 150° C. As for the solvent, there can be used acetonitrile, water, ethanol, pyridine, dimethyl sulfoxide, 1-methyl-2-pyrrolidone, etc. As for the base, there is employed such one as functions as an acid acceptor, and concrete examples of such a base include triethylamine, 1,8-diazabicyclo[5.4.0]-7-undecene, and carbonates such as sodium carbonate and sodium bicarbonate. Compound (III) may be used in excess so that it may also act as an acid acceptor.

Compounds (II), which are used as raw materials, are also novel, and can be prepared, for example, by the following ring closing reaction.

(b) Ring closing reaction

Compounds (I) of this invention and their salts can be prepared by subjecting a compound represented by the following formula (IV)

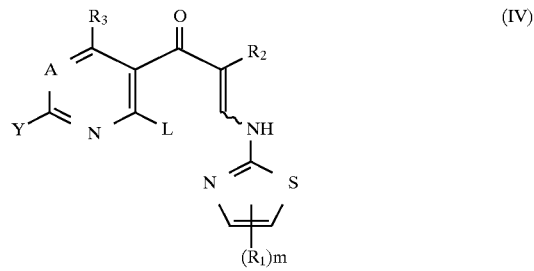

wherein L is an eliminable group, and $R_1$, $R_2$, R3, A, Y and m are as defined above to ring closing reaction.

As to the eliminable group L, there can be employed the same groups as those included in the definition of Y, as is explained in the above with regard to formula (II).

This ring closing reaction can be conducted by stirring a mixture of Compound (IV) with a solvent in the presence of a base such as potassium carbonate, sodium carbonate, sodium hydride, potassium t-butoxide or potassium fluoride, the amount of which base is one to three times in mole as much as Compound (IV), at a temperature ranging from 30° to 150° C., preferably 30° to 100° C., for 1 to 6 hours. Examples of suitable solvent include ethanol, dioxane, tetrahydrofuran, dimethylformamide, dimethyl sulfoxide, etc.

Compounds (IV), which are used as raw materials, are also novel, and can be prepared according to the processes in Examples which are described later.

(c) Oxidation reaction

Compounds of this invention represented by formula (I) and salts thereof can be prepared by subjecting a compound represented by the following formula (V)

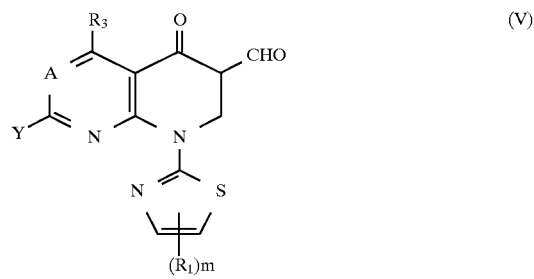

wherein $R_1$, $R_3$, A, Y and m are as defined above to an oxidation reaction.

This oxidation reaction is carried out by mixing the above Compound (V) with an oxidizer in a solvent and stirring the resulting mixture for several hours at a temperature of 100° C. or lower, preferably 0° to 50° C. Examples of the oxidizer include 2,3-dichloro-5,6-dicyanobenzoquinone, tetrachloro-1,4-benzoquinone, tetracyanoethylene, palladium-carbon, N-bromosuccinimide and manganese dioxide. As for examples of the solvent, there can be taken 1,4-dioxane, toluene, xylene, ethanol, t-butanol, ethyl acetate, dimethylformamide, etc.

Compounds (I) of this invention and salts thereof can also be prepared by making Compound (I) of this invention wherein Z is a hydrogen atom react with amino acid or peptide according to a usual method, or by aminating Compound (I) wherein $R_3$ is a halogen atom so as to convert said compound into a compound wherein $R_3$ is an amino group.

When the compounds of this invention obtained in the above-mentioned manner are ester forms, said compounds can be converted into carboxylic acid forms by means of hydrolyzing the ester parts by a usual method. Further, the carboxylic acid parts of Compounds (I) can also be esterified by a usual method. Furthermore, when Z of the compounds of this invention is an amino acid residue or peptide residue protected by a protecting group, said protecting group can be eliminated by a usual method.

The compounds of this invention thus prepared can be isolated and purified by usual processes. According to the conditions of isolation and purification, these compounds are obtained in the form of salts, free carboxylic acids or free amines, which are then converted from one into another in accordance with purposes, and, thus, there can be obtained compounds in desired forms.

When the compounds of this invention are racemic, they can, if necessary, be separated into respective optical isomers by known methods. The stereoisomers (cis form and trans form) of the compounds of this invention can, if necessary, be separated from one another according to a usual method such as, for example, a fractional crystallization method or a chromatography method.

It is of course possible to use an optical isomer or a stereoisomer as a raw material and lead it to a desired substance corresponding thereto, and such a method is generally advantageous.

Examples

This invention is detailedly explained by working examples below.

In the following, Examples of Series A include specific examples of processes for the preparation of intermediates (II) [general formula (II)], Examples of Series B include specific examples of processes for the preparation of raw materials (III) [general formula (III)], Examples of Series C include specific examples of processes for the preparation of object substances (I-a), and Examples of Series D include specific examples of processes for the preparation of pharmaceutical preparations.

Further, the attached FIGS. 15–19 show reaction formulae of the reactions which are mentioned in the following Examples of Series A, Series B and Series C-14.

1. Series A

Example A-1 Preparation of intermediate (II) 7-chloro-1,4-dihydro-4-oxo-1-(2-thiazolyl)-1,8-naphthyridine-3-carboxylic acid ethyl ester (1)-1 2,6-Dichloropyridine (20 g) was dissolved in tetrahydrofuran (200 ml), and, to the resulting solution, there was added dropwise a solution of n-butyllithium (1.6M) in n-hexane (84.5 ml) in a flow of argon gas at a temperature of −78° C. over a period of 30 minutes. After the resulting solution was stirred for one hour at the same temperature, greatly excess carbon dioxide (solid) was added. After stirring for one hour, temperature was raised to −10° C., and, then, water and hydrochloric acid were added in order so that pH might be 1–2, and, thereafter, the resultant solution was extracted with ethyl acetate. After the obtained extract was dried over anhydrous sodium sulfate, solvent was distilled off under reduced pressure to dryness. To the obtained solid, there was added thionyl chloride (40 ml), and the resulting mixture was heated to reflux for three hours. The excess thionyl chloride was distilled off under reduced pressure, and, then, crude product was distilled under reduced pressure to form 2,6-dichloronicotinoyl chloride (19.8 g).

Boiling point: 97°–99° C./1 mmHg

IR (neat) $cm^{-1}$: 1784

(1)-2 A mixture of 2,6-dichloronicotinic acid (50.6 g) with thionyl chloride (100 ml) was refluxed for 2 hours. The excess thionyl chloride was distilled off under reduced pressure, and crude product was distilled under reduced pressure to give 2,6-dichloronicotinoyl chloride (44.9 g).

Boiling point: 115°–120° C./3 mmHg

IR (neat) $cm^{-1}$: 1784

(2) Ethoxymagnesiummalonic acid diethyl ester derived from metal magnesium (5.36 g), malonic acid diethyl ester (35.4 g) and ethanol (27 ml) was dissolved in a mixed solution composed of tetrahydrofuran (35 ml) and toluene (140 ml). The resultant solution was cooled with ice, and, to this solution under stirring, there was added dropwise a mixed solution composed of tetrahydrofuran (19 ml) and toluene (32 ml) containing the acid chloride (44.9 g) obtained in the above (1)-1 or (1)-2. After completion of the dropwise addition, the obtained mixture was stirred overnight at room temperature. The mixture was concentrated under reduced pressure, and aqueous solution of hydrochloric acid was added to the residue, and, then, the mixture was extracted with ethyl acetate. The obtained extract was dried over anhydrous sodium sulfate, and the solvent was distilled off under reduced pressure, and, thus, there was produced an oily material. Water (190 ml) and p-toluenesulfonic acid (0.1 g) were added to the oily material, and the mixture was refluxed for 2 hours. After cooled, the mixture was extracted with chloroform and dried over anhydrous sodium sulfate, and then, the solvent was distilled off under reduced pressure to give an oily material. The obtained crude product was distilled under reduced pressure to produce 2,6-dichloronicotinoylacetic acid ethyl ester (45.2 g).

Boiling point: 135°–140° C./2 mmHg (3) A mixture of the compound (44.9 g) obtained in the above (2), acetic anhydride (43.8 g) and ethyl orthoformate (37.7 g) was refluxed for one hour. The mixture was concentrated to dryness under reduced pressure, and, under ice cooling, diisopropyl ether (500 ml) and 2-aminothiazole (20 g) were added, and then, the resulting mixture was stirred at room temperature for 5 hours. The crystals were taken by filtration to give 2-(2,6-dichloronicotinoyl )-3-(2-thiazolyl-amino)acrylic acid ethyl ester (52.8 g).

Melting point: 119°–122° C. (recrystallized from diisopropyl ether)

IR (KBr) $cm^{-1}$: 1700

(4) The compound (51.7 g) obtained in the above (3) was dissolved in dioxane (310 ml), and, then, potassium carbonate (21.4 g) was added, and the resulting mixture was stirred at 60° C. for one hour. After ice water was added, the mixture was neutralized with 10% aqueous solution of hydrochloric acid, and the crystals were taken by filtration. The crystal s were recrystallized from a mixed solution composed of chloroform and diisopropyl ether to give 7-chloro-1,4-dihydro-4-oxo-1-(2-thiazolyl)-1,8-naphthyridine-3-carboxylic acid ethyl ester (44.6 g).

Melting point: 176°–177° C.

IR (KBr) cm$^{-1}$: 1724

NMR (CDCl$_3$) δ: 1.43 (t, 3H, J=6.5 Hz), 4.45 (q, 2H, J=6.5 Hz), 7.38 (d, 1H, J=3.5 Hz), 7.52 (d, 1H, J=8.5 Hz), 7.75 (d, 1H, J=3.5 Hz), 8.78 (d, 1H, J=8.5 Hz), 10.00 (s, 1H)

Example A-2 Preparation of intermediate (II) 7-chloro-1-(4-fluoro-2-thiazolyl)-1,4-dihydro-4-oxo-1,8-naphthyridine-3-carboxylic acid ethyl ester A mixture composed of the ester (250 mg) obtained in Example 1 (4), N-fluoro-2,6-dichloro-pyridinium tetrafluoroborate (240 mg) and 1,2-dichloroethane (10 ml) was heated to reflux for two days.

Water was added to the reaction solution, and the resultant solution was extracted with chloroform. After the obtained extract was dried over anhydrous sodium sulfate, solvent was distilled off under reduced pressure. The obtained residue was purified by silica gel column chromatography (eluent: chloroform), and the above-identified compound (40 mg) was obtained by recrystallization from ethyl acetate.

Melting point: 174°–175° C.

IR (KBr) cm$^{-1}$: 1700

NMR (CDCl$_3$) δ: 1.42 (t, 3H, J=6.5 Hz), 4.45 (q, 2H, J=6.5 Hz), 7.33 (d, 1H, J=3.5 Hz), 7.51 (d, 1H, J=8.5 Hz), 8.78 (d, 1H, J=8.5 Hz), 9.85 (s, 1H)

Example A-3 Preparation of intermediate (II) 5,7-dichloro-1,4-dihydro-4-oxo-1-(2-thiazolyl)-1,8-naphthyridine-3-carboxylic acid (1) To a mixture composed of 4-amino-2,6-dichloropyridine (5.5 g), cuprous chloride (4.4 g) and concentrated hydrochloric acid (50 ml), sodium nitrite (3.5 g) was added little by little under cooling with ice and sodium chloride. After the resultant mixture was stirred for one hour at the same temperature and for one and a half hour at a room temperature, water was added, and the mixture was extracted with chloroform. After the obtained extract was dried over anhydrous sodium sulfate, solvent was distilled off under reduced pressure to give 2,4,6-trichloropyridine (5.5 g).

IR (neat) cm$^{-1}$: 1563, 1357, 1155, 851, 823

NMR (CDCl$_3$) δ: 7.31 (s, 2H)

(2) To a mixture composed of the compound (5.5 g) obtained in the above (1) and tetrahydrofuran (55 ml), there was added dropwise a solution of n-butyllithium (1.6M) in n-hexane (20 ml) at a temperature of –78° C. After the resulting solution was stirred for one hour at the same temperature, greatly excess carbon dioxide (solid) was added. After stirring for one hour, temperature was raised to 0° C., and, then, an aqueous solution of hydrochloric acid was added so that the solution might be acidic, and, thereafter, the resultant solution was extracted with ethyl acetate. After the obtained extract was dried over anhydrous sodium sulfate, solvent was distilled off under reduced pressure. To the obtained residue, there was added diisopropyl ether, and crystals were taken by filtration, and, thus, there was obtained 2,4,6-trichloronicotinic acid (6.5 g).

Melting point: 138°–141° C.

IR (KBr) cm$^{-1}$: 1715

(3) A mixture of the compound (6.5 g) obtained in the above (2) with thionyl chloride (25 ml) was refluxed for three hours. Excessive thionyl chloride was distilled off under reduced pressure, and crude product was distilled under reduced pressure to give 2,4,6-trichloronicotinoyl chloride (6.6 g).

Boiling point: 93°–95° C./1 mmHg

IR (neat) cm$^{-1}$: 1791

(4) A solution of methylmagnesium bromide (3M) dissolved in ether (19 ml) was added dropwise at a temperature of 0° C. to a mixture composed of malonic acid monoethyl ester (3.6 g) and tetrahydrofuran (30 ml). After the resultant solution was stirred for one hour at room temperature, a mixture composed of the compound (6.6 g) obtained in the above (3) and tetrahydrofuran (30 ml) was added dropwise, and the resulting solution was heated at 60° C. for one hour and a half. Solvent was distilled off under reduced pressure, and aqueous solution of hydrochloric acid was added to the obtained residue, and, then, the mixture was extracted with chloroform. The obtained extract was dried over anhydrous sodium sulfate, and the solvent was distilled off under reduced pressure, and, then, the obtained crude product was distilled under reduced pressure to produce 2,4,6-trichloronicotinoylacetic acid ethyl ester (4.8 g).

Boiling point: 160°–162° C./2 mmHg

IR (neat) cm$^{-1}$: 1746

(5) A mixture of the compound (4.8 g) obtained in the above (4), acetic anhydride (4.2 g) and ethyl orthoformate (3.6 g) was refluxed for one hour and a half. The mixture was concentrated to dryness under reduced pressure, and, under ice cool ing, diisopropyl ether (100 ml) and 2-aminothiazole (1.6 g) were added, and then, the resulting mixture was stirred at room temperature for three hours. Solvent was distilled off under reduced pressure, and the obtained residue was purified by silica gel column chromatography (eluent: chloroform), and, thus, 2-(2,4,6-trichloronicotinoyl)-3-(2-thiazolyl-amino)acrylic acid ethyl ester (4.0 g) was produced by recrystallization from ethyl acetate.

Melting point: 126°–127° C.

IR (KBr) cm$^{-1}$: 1691

(6) A mixture composed of the compound (4.0 g) obtained in the above (5), potassium carbonate (1.5 g) and ethyl acetate (40 ml) was heated at 60° C. for one hour. Solvent was distil led off under reduced pressure, and water was added to the obtained residue, and, then, the resultant mixture was extracted with chloroform. The obtained extract was dried over anhydrous sodium sulfate, and the solvent was distilled off under reduced pressure, and, then, the obtained residue was purified by silica gel column chromatography (eluent: chloroform), and, thus, 5,7-dichloro-1,4-dihydro-4-oxo-1-(2-thiazolyl)-1,8-naphthyridine-3-carboxylic acid ethyl ester (2.5 g) was obtained by recrystallization from chloroform.

Melting point: 226°–227° C.

IR (KBr) cm$^{-1}$: 1737, 1692

(7) A mixture of the ester (1.8 g) obtained in the above (6) with 20% aqueous solution of hydrochloric acid (60 ml) was heated to reflux for five hours. After the mixture was cooled, water was added, and crystals were taken by filtration, and then, the crystals were washed with water to give the above-identified 5,7-dichloro-1,4-dihydro-4-oxo-1-(2-thiazolyl)-1,8-naphthyridine-3-carboxylic acid (1.4 g).

Melting point: 264°–266° C.

IR (KBr) cm$^{-1}$: 1729

Example A-4 Preparation of intermediate (II) 5-amino-7-chloro-1,4-dihydro-4-oxo-1-(2-thiazolyl)-1,8-naphthyridine-3-carboxylic acid (1) A mixture of the compound (500 mg) obtained in Example A-3 (6), benzylamine (140 mg), triethylamine (280 mg) and toluene (15 ml) was refluxed for 30 minutes. Solvent was distilled off under reduced pressure, and water was added to the obtained residue, and, then, the resultant mixtu re was extracted with chloroform. The obtained extract was dried with anhydrous sodium sulfate, and then, the solvent was distilled off under reduced pressure. The obtained residue was subjected to recrystallization from ethyl acetate, and, thus, 5-benzylamino-7-chloro-1,4-dihydro-4-oxo-1-(2-thiazolyl)-1,8-naphthyridine-3-carboxylic acid ethyl ester (510 mg) was produced.

Melting point: 141°–143° C.

IR (KBr) cm$^{-1}$: 1733

NMR (CDCl$_3$) δ: 1.42 (t, 3H, J=7 Hz), 4.41 (q, 2H, J=7 Hz), 4.49 (d, 2H, J=6.5 Hz), 6.47 (s, 1H), 7.31 (d, 1H, J=3.5 Hz), 7.32–7.40 (m, 5H), 7.70 (d, 1H, J=3.5 Hz), 9.87 (s, 1H), 11.2–11.7 (m, 1H)

(2) A mixture composed of the ester (1.0 g) obtained in the above (1), concentrated sulfuric acid (2 ml) and acetic acid (8 ml) was stirred at 110° C. for five hours. After cooling, 8 ml of water was added, and then, the mixture was stirred at 110° C. for one hour. Crystals were taken out by filtration and washed with water to give 740 mg of the above-identified compound.

Melting point: 264°–265° C.

IR (KBr) cm$^{-1}$: 1727

Example A-5 Preparation of intermediate (II) 7-chloro-1,4-dihydro-4-oxo-1-(2-thiazolyl)-5-trifluoromethyl-1,8-naphthyridine-3-carboxylic acid ethyl ester (1) A mixture of 2,6-dichloro-4-trifluoromethylpyridine (5 g) with tetrahydrofuran (50 ml) was cooled to −78° C., and a solution of n-butyllithium (1.6M) in n-hexane (16 ml) was added dropwise to the mixture, which was then stirred for 30 minutes. Then, greatly excessive carbon dioxide (solid) was added to this mixture, which was subsequently stirred for one hour. After the temperature was raised up to 0° C., the mixture was extracted with ethyl acetate and dilute hydrochloric acid, and the resultant orgnaic layer was dried over sodium sulfate. Solvent was distilled off under reduced pressure, and thionyl chloride (20 ml) was added to the obtained residue, and then, the resulting mixture was heated to reflux for six hours. Excess thionyl chloride was distilled off under reduced pressure, and then, the obtained residue was distilled under reduced pressure to give 2,6-dichloro-4-trifluoromethylnicotinoyl chloride (3.8 g).

Boiling point: 77°–78° C./2 mmHg

IR (neat) cm$^{-1}$: 1797

(2) A drop of carbon tetrachloride was added to a mixture of magnesium (0.36 g) with ethanol (1.5 ml), and then, a mixture composed of diethyl malonate (2.4 g), ethanol (1.5 ml) and toluene (10 ml) was added dropwise to the above mixture, which was subsequently stirred for two hours. After the mixture was cooled with ice, a mixture composed of the compound (3.8 g) obtained in the above (1) and tetrahydrofuran (10 ml) was added dropwise to the mixture, which was then stirred for three hours at room temperature. Then, the mixture was extracted with ethyl acetate and dilute hydrochloric acid, and the resultant orgnaic layer was dried over sodium sulfate. Solvent was distilled off under reduced pressure, and water (20 ml) and p-toluenesulfonic acid (50 mg) were added to the obtained residue, and then, the resulting mixture was heated to reflux for three hours. The mixture was subsequently extracted with chloroform and water, and the resultant orgnaic layer was dried over sodium sulfate. Solvent was distilled off under reduced pressure to give 2,6-dichloro-4-trifluoromethyl-nicotinoyl acetic acid ethyl ester (0.9 g).

IR (neat) cm$^{-1}$: 1744, 1721

MS (m/z): 330 (MH$^+$)

(3) A mixture composed of the compound (0.9 g) obtained in the above (2), ethyl orthoformate (0.6 g) and acetic anhydride (0.7 g) was heated to reflux for 1.5 hours at 140° C., and then was concentrated to dryness under reduced pressure. Isopropyl ether (20 ml) was added to the obtained residue, and then, under ice cooling, 2-aminothiazol (0.3 g) was added. After stirring for three hours at room temperature, solvent was distilled off. To this residue, chloroform and water were added for extraction, and the resultant orgnaic layer was dried over sodium sulfate. Solvent was distilled off under reduced pressure, and the obtained residue was purified by silica gel column chromatography (eluent: chloroform) to give 2-(2,6-dichloro-4-trifluoromethylnicotinoyl)-3-(2-thiazolylamino)acrylic acid ethyl ester (0.37 g).

IR (neat) cm$^{-1}$: 1713

MS (m/z): 440 (MH$^+$)

(4) A mixture composed of the compound (0.37 g) obtained in the above (3), potassium carbonate (0.13 g) and ethyl acetate (10 ml) was heated to reflux for 15 minutes. Ethyl acetate and water were added to the mixture for extraction, and the resultant orgnaic layer was dried over sodium sulfate. Solvent was distilled off under reduced pressure, and the obtained residue was subjected to recrystallization from ethyl acetate, and thus, the above-identified 7-chloro-1,4-dihydro-4-oxo-1-(2-thiazolyl)-5-trifluoromethyl-1,8-naphthyridine-3-carboxylic acid ethyl ester (0.27 g) was obtained.

Melting point: 184°–185° C.

IR (KBr) cm$^{-1}$: 1736, 1703

Example A-6 Preparation of intermediate (II) 5,8-dihydro-2-methanesulfonyl-5-oxo-8-(2-thiazolyl)pyrido[2,3-d]pyrimidine-6-carboxylic acid ethyl ester (1) A solution of malonic acid monoethyl ester (12.3 g) dissolved in tetrahydrofuran (80 ml) was cooled with ice, and then, to the resulting solution, a solution of methylmagnesium bromide (3M) in ether (64 ml) was added dropwise. After the resultant mixture was stirred for 20 minutes, a solution of 2-methylthio-4-chloropyrimidine-5-carbonylchloride (8.6 g) dissolved in tetrahydrofuran (100 ml) was added dropwise to the mixture, which was then stirred for two hours at a room temperature. This reaction mixture was poured into ice water, and then, concentrated hydrochloric acid was added to the resulting solution so that pH might be adjusted to be 5–6, and the solution was subsequently extracted with ethyl acetate. The obtained extract was dried over anhydrous sodium sulfate, and solvent was distilled off under reduced pressure. Then, purification was conducted by silica gel column chromatography (eluent: chloroform), and thus, 3-(2-methylthio-4-chloropyrimidin-5-yl)-3-oxopropionic acid ethyl ester (8.0 g) was obtained.

IR (neat) cm$^{-1}$: 1743

MS (m/z): 275 (MH$^+$)

(2) A mixture composed of the compound (7.95 g) obtained in the above (1), orthoethyl formate (6.80 g) and acetic anhydride (7.76 g) was heated to reflux at 130° C. for one hour, and then was concentrated under reduced pressure. Under ice cooling, diisopropyl ether (100 ml) and 2-aminothiazol (3.28 g) were added to the mixture, which was then stirred over night at room temperature. Crystal was taken by filtration and then was washed with diisopropyl ether. This crystal was dissolved in 1,4-dioxane (70 ml), and, to the resulting solution under ice cooling, potassium carbonate (2.72 g) was added, and the resulting mixture was stirred at room temperature for five hours. This mixture was cooled with ice, and ice water (200 ml) was added to the mixture, which was then neutralized with 10% aqueous solution of hydrochloric acid. Crystal was taken by filtration, and the crystal was washed with water, 1,4-dioxane and diisopropyl ether successively, and, thus, 5,8-dihydro-2-methylthio-5-oxo-8-(2-thiazolyl)pyrido[2,3-d]pyrimidine-6-carboxylic acid ethyl ester (6.0 g) was obtained.

Melting point: 183°–184° C.

IR (KBr) cm$^{-1}$: 1736

(3) A solution of the compound (5.99 g) obtained in the above (2) dissolved in methylene chloride (450 ml) was cooled with ice, and, to the resulting mixture, 80% m-chloroperbenzoic acid (9.30 g) was added little by little, and the resultant mixture was stirred over night at room temperature. The mixture was then washed with an aqueous solution of sodium thiosulfate, an aqueous solution of sodium hydrogencarbonate and a saturated aqueous solution of sodium chloride successively. After the mixture was dried over sodium sulfate, solvent was distilled off under reduced pressure. Then, the above-identified 5,8-dihydro-2-methanesulfonyl-5-oxo-8-(2-thiazolyl)pyrido[2,3-d]pyrimidine-6-carboxylic acid ethyl ester (4.48 g) was obtained by recrystallization from a mixed solution composed of ethyl acetate and diisopropylether.

Melting point: 185°–187° C.

IR (KBr) cm$^{-1}$: 1741

2. Series B

Example B-1 Preparation of raw material compound (III) Trans-3-(N-t-butoxycarbonylmethylamino)-4-methylpyrrolidine (1) Trans-3-amino-1-benzyl-4-methylpyrrolidine (19 g) was dissolved in methylene chloride (200 ml), and, to the resulting solution, a solution of di-t-butyl dicarbonate (22.9 g) in methylene chloride (20 ml) was added under ice cooling. The resultant mixture was stirred at room temperature for one hour. Then, this reaction solution was concentrated under reduced pressure to give trans-1-benzyl-3-(t-butoxycarbonylamino)-4-methylpyrrolidine (28.2 g)

Melting point: 138°–140° C. (recrystallized from ethyl acetate-n-hexane)

IR (KBr)cm$^{-1}$: 3198, 1706

MS (m/z): 291 (MH$^+$)

(2) A 70% toluene solution (40 ml) of sodium bis(2-methoxyethoxy)aluminum hydride was dissolved in 150 ml of toluene, and, to the resulting solution, the compound (10 g) obtained in the above (1) was added little by little under ice cooling. The obtained reaction mixture was heated to reflux for one hour, and, after ice cooling, excess reagent was decomposed with water. Then, insoluble substance was separated by filtration, and the obtained filtrate was dried over anhydrous magnesium sulfate, and solvent was distilled off under reduced pressure. The resultant residue was dissolved in methylene chloride (100 ml), and to the resulting solution, there was added under ice-cooling a solution of di-t-butyl dicarbonate (7.5 g) in methylene chloride (10 ml). The obtained mixture was stirred at room temperature for 3.5 hours, and then, was concentrated under reduced pressure. The resultant residue was purified by silica gel column chromatography (eluent n-hexane:ethyl acetate=5:1) to give trans-1-benzyl-3-(N-t-butoxycarbonylmethylamino)-4-methyl-pyrrolidine (9.9 g)

IR (neat)cm$^{-1}$: 1694

MS (m/z): 305 (MH$^+$)

(3) The compound (1.52 g) obtained in the above (2) was dissolved in ethanol (50 ml), and, to the resulting solution, there was added 10% palladium carbon (200 mg), and was absorbed a theoretical amount of hydrogen at 50° C. After the catalyst was separated by filtration, solvent was distilled off under reduced pressure, and thus, trans-3-(N-t-butoxycarbonylmethylamino)-4-methylpyrrolidine (950 mg) was obtained.

IR (neat)cm$^{-1}$: 3337, 1685

MS (m/z): 215 (MH$^+$)

Example B-2 Preparation of raw material compound (III) (+)-Trans-3-(N-t-butoxycarbonylmethylamino)-4-methoxypyrrolidine (1) Trans-3-amino-1-benzyl-4-methoxypyrrolidine (racemic; 22.4 g) disclosed in Japanese Laid-open Patent Publication No. 69474/1990 and 19.6 g of L-tartaric acid were dissolved in methanol (350 ml), and the resulting solution was left still at room temperature for 7 hours. Precipitated L-tartrate was taken by filtration, and then, was subjected to recrystallization with methanol and water, and thus, there was obtained trans-3-amino-1-benzyl-4-methoxypyrrolidine L-tartrate (14.1 g) having the following physical properties. Then, all the mother liquors were put together, and the solvent was distilled off under reduced pressure, and then, a saturated brine was added, and, subsequently, potassium carbonate was added so that the obtained mixture might become basic. Then, the mixture was extracted with ethyl acetate. The obtained extract was washed with saturated brine, and was then dried over anhydrous sodium sulfate, and solvent was distilled off under reduced pressure. The resultant residue and D-tartaric acid (6.73 g) were dissolved in methanol (180 ml), and the obtained solution was left still at room temperature for 7 hours. Precipitated D-tartrate was taken by filtration, and was then subjected to recrystallization with methanol and water, and thus, there was obtained trans-3-amino-1-benzyl-4-methoxypyrrolidine D-tartrate (9.9 g) having the following physical properties.

L-tartrate

Melting point: 206°–208° C. (decomposed)

[a]$_D^{29}$+33.0° (c=1.003, water)

Elementary analysis (%): as $C_{12}H_{18}N_2O.\frac{3}{2} C_4H_6O_6$

Calculated value: C, 50.11; H, 6.31; N, 6.49

Found value: C, 49.85; H, 6.26; N, 6.27 D-tartrate

Melting point: 207°–209° C. (decomposed)

[a]$_D^{29}$−33.4° (c=1.020, water)

Elementary analysis (%): as $C_{12}H_{18}N_2O.\frac{3}{2}C_4H_6O_6$

Calculated value: C, 50.11; H, 6.31; N, 6.49

Found value: C, 50.35; H, 6.32; N, 6.47

(2) Saturated brine was added to the L-tartrate (3.65 g) obtained in the above (1), and the resulting mixture was neutralized with potassium carbonate, and was then extracted with ethyl acetate. The obtained extract was washed with saturated brine, and was subsequently dried over anhydrous sodium sulfate. Then, solvent was distilled off under reduced pressure, and thus, there was obtained (+)-trans-3-amino-1-benzyl-4-methoxypyrrolidine (1.23 g).

[a]$_D^{27}$+32.2° (c=1.053, methanol)

(3) The compound (5.74 g) obtained in the above (2) was dissolved in methanol (65 ml), and, under ice cooling, di-t-butyl dicarbonate (7.29 g) was added to the resulting solution, which was then stirred at the same temperature for 30 minutes, and at room temperature for 4 hours. Solvent was distilled off under reduced pressure, and the resultant residue was purified by silica gel column chromatography (eluent chloroform:methanol=50:1), and thus, there was obtained (+)-trans-1-benzyl-3-(t-butoxycarbonylamino)-4-methoxypyrrolidine (8.55 g).

Melting point: 44°–45° C.

[a]$_D^{29}$+9.5° (c=1.044, methanol)

(4) Lithium aluminum hydride (3.43 g) was suspended in anhydrous tetrahydrofuran (150 ml), and, to the resulting suspension, an anhydrous tetrahydrofuran solution (50 ml) of the compound (8.4 g) obtained in the above (3) was added dropwise, and the resultant mixture was stirred at room temperature for one hour. After the mixture was refluxed for 5 hours, excess reagent was decomposed with water under ice cooling, and then, insoluble substance was removed by filtration. Then, the obtained filtrate was extracted with ethyl acetate. The resultant extract was washed with saturated brine, and was then dried over anhydrous sodium sulfate. Solvent was distilled off under reduced pressure, and the obtained residue was dissolved in methylene chloride (180 ml), and, to the resultant solution, di-t-butyl dicarbonate (6.3 g) was added under ice cooling. The resultant mixture was stirred at the same temperature for 30 minutes, and at room temperature for 2 hours, and then, solvent was distilled off under reduced pressure. The resultant residue was purified by silica gel column chromatography (eluent chloroform:methanol=50:1), and thus, there was obtained (+)-trans-1-benzyl-3-(N-t-butoxycarbonylmethylamino)-4-methoxypyrrolidine (8.26 g).

$[a]_D^{29}$+9.9° (c=1.002, methanol)

(5) The desired (+)-trans-3-(N-t-butoxycarbonylmethylamino)-4-methoxypyrrolidine (5.59 g) was obtained from the compound (8.15 g) produced in the above (4), in the same manner as in Example B-1 (3).

$[a]_D^{29}$+12.5° (c=1.051, methanol)

IR (neat) cm$^{-1}$: 3318, 1693

MS (m/z): 231 (MH$^+$)

Example B-3 Preparation of raw material compound (III) (−)-Trans-3-(N-t-butoxycarbonylmethylamino)-4-methoxypyrrolidine (1) (−)-Trans-3-amino-1-benzyl-4-methoxypyrrolidine (1.01 g) was obtained from the D-tartrate (2.57 g) produced in Example B-2 (1), in the same manner as in Example B-2 (2).

$[a]_D^{27}$−32.7° (c=1.016, methanol)

(2) (−)-Trans-1-benzyl-3-(t-butoxycarbonylamino)-4-methoxypyrrolidine (4.5 g) was obtained from the compound (3.03 g) produced in the above (1), in the same manner as in Example B-2 (3).

Melting point: 44–45° C.

$[a]_D^{29}$−9.5° (c=1.080, methanol)

(3) (−)-Trans-1-benzyl-3-(N-t-butoxycarbonylmethylamino)-4-methoxypyrrolidine (4.25 g) was obtained from the compound (4.25 g) produced in the above (2), in the same manner as in Example B-2 (4).

$[a]_D^{29}$−10.1° (c=1.054, methanol)

(4) The desired (−)-trans-3-(N-t-butoxycarbonylmethylamino)-4-methoxypyrrolidine (2.81 g) was obtained from the compound (4.25 g) produced in the above (3), in the same manner as in Example B-2 (5).

$[a]_D^{29}$−12.2° (c=1.003, methanol)

IR (neat) cm$^{-1}$: 3318, 1693

MS (m/z): 231 (MH$^+$)

Example B-4 Preparation of raw material compound (III) 3-(N-t-butoxycarbonylmethylamino)-3-methylpyrrolidine (1) 1-Benzyl-3-(N-t-butoxycarbonylamino)-3-methylpyrrolidine (28.3 g) was obtained from 3-amino-1-benzyl-3-methylpyrrolidine (20 g) in the same manner as in Example B-1 (1).

IR (neat) cm$^{-1}$: 3356, 1716, 1697

MS (m/z): 291 (MH$^+$)

(2) 1-Benzyl-3-(N-t-butoxycarbonylmethylamino)-3-methylpyrrolidine (7.5 g) was obtained from the compound (11.4 g) produced in the above (1), in the same manner as in Example B-1 (2).

IR (neat) cm$^{-1}$: 1697

MS (m/z): 305 (MH$^+$)

(3) The desired 3-(N-t-butoxycarbonylmethylamino)-3-methylpyrrolidine (5.5 g) was obtained from the compound (7.5 g) produced in the above (2), in the same manner as in Example B-1 (3).

IR (neat) cm$^{-1}$: 3337, 1682

MS (m/z): 215 (MH$^+$)

3. Series C

Example C-1 Preparation of desired product (I) 1,4-Dihydro-7-(trans-3-methoxy-4-methylamino-1-pyrrolidinyl)-4-oxo-1-(2-thiazolyl)-1,8-naphthyridine-3-carboxylic acid, its salt and its L-Ala derivative (1) Triethylamine (18 ml) was added to a suspension composed of 7-chloro-1,4-dihydro-4-oxo-1-(2-thiazolyl)-1,8-naphthyridine-3-carboxylic acid ethyl ester (7.1 g) obtained in Example A-1 (4), trans-3-methoxy-4-methylaminopyrrolidine dihydrochloride (6.0 g) and acetonitrile (150 ml). The resulting reaction mixture was stirred at room temperature for 5 hours, and was then concentrated under reduced pressure. Then, an aqueous solution of sodium hydrogencarbonate was added, and the resultant mixture was extracted with chloroform. After the obtained extract was dried over anhydrous sodium sulfate, solvent was distilled off under reduced pressure, and the resultant residue was purified by silica gel column chromatography (eluent chloroform:methanol=6:1), and thus, there was obtained 1,4-dihydro-7-(trans-3-methoxy-4-methylamino-1-pyrrolidinyl)-4-oxo-1-(2-thiazolyl)-1,8-naphthyridine-3-carboxylic acid ethyl ester (6.1 g).

Melting point: 73°–76° C.

(2) A solution composed of the above ester (6.0 g) nd an 18% aqueous solution of hydrochloric acid (100 ml) was stirred at 100° C. for 28 hours. Crystals were taken by filtration, and washed with a mixed solution composed of ethanol and diisopropyl ether to give 1,4-dihydro-7-(trans-3-methoxy-4-methylamino-1-pyrrolidinyl)-4-oxo-1-(2-thiazolyl)-1,8-naphthyridine-3-carboxylic acid hydrochloride (Compound 1–1)(4.45 g).

Melting point: 270°–273° C.

(3) A solution composed of the hydrochloride (51.5 g) obtained in the above (2), water (500 ml) and aqueous ammonia (40 ml) was stirred overnight at 50° C. Acetonitrile was added to this solution, which was then concentrated under reduced pressure, and crystals were taken by filtration. The crystals were washed with water and acetonitrile to give 1,4-dihydro-7-(trans-3-methoxy-4-methylamino-1-pyrrolidinyl)-4-oxo-1-(2-thiazolyl)-1,8-naphthyridine-3-carboxylic acid (Compound 1-1-1)(32.6 g).

Melting point: 290°–292° C. (decomposed)

(4) A mixture composed of the compound (2.0 g) obtained in the above (3), lactic acid (3.1 g) and distilled water (4 ml) was heated at 60° C. to be dissolved. After the resultant solution was cooled to room temperature, ethanol (70 ml) was added, and crystals were taken by filtration and washed with ethanol to give 2 g of a lactate (Compound 1-1-2).

Melting point: 288°–291° C. (decomposed)

(5) To a mixture composed of the ester (1.89 g) obtained in the above (1), N-t-butoxycarbonyl-L-alanine (1.26 g) and methylene chloride (80 ml), there was added 1.27 g of 1-ethyl-3-(3-dimethylaminopropyl)carbodiimide hydrochloride (WSC), and the resultant mixture was stirred at room temperature for 3 hours. After washed with water, the mixture was dried over anhydrous sodium sulfate, and was then concentrated under reduced pressure. The resulting concentrate was purified by silica gel column chromatography (eluent chloroform:methanol=50:1) to give 7-{trans-3-[N-(N-t-butoxycarbonyl-L-alanyl)]methylamino-4-methoxy-1-pyrrolidinyl}-1,4-dihydro-4-oxo-1-(2-thiazolyl)-1,8-naphthyridine-3-carboxylic acid ethyl ester (2.15 g).

Melting point: 120°–123° C.

[a]$_D^{28}$+10.2° (c=1.0, chloroform)

A mixture composed of this ethyl ester (1.71 g), 0.5N hydrochloric acid (42 ml) and ethanol (22 ml) was stirred under heating at 80° C. for 17.5 hours. The resultant solution was concentrated under reduced pressure, and crystals were taken by filtration, and were then washed with 10% hydrochloric acid and ethanol to give 1.16 g of 7-[trans-3-(N-L-alanylmethylamino)-4-methoxy-1-pyrrolidinyl]-1,4-dihydro-4-oxo-1-(2-thiazolyl)-1,8-naphthyridine-3-carboxylic acid hydrochloride (Compound 1-1-3).

Melting point: 230°–233° C.

[a]$_D^{29}$+8.40 (c=1.0, water)

Example C-2 Preparation of desired compound (I) (+)-1,4-Dihydro-7-(trans-3-methoxy-4-methylamino-1-pyrrolidinyl)-4-oxo-1-(2-thiazolyl)-1,8-naphthyridine-3-carboxylic acid (Compound 1-2-1) and its hydrochlorid (Compound 1-2)

(1) With use of 7-chloro-1,4-dihydro-4-oxo-1-(2-thiazolyl)-1,8-naphthyridine-3-carboxylic acid ethyl ester obtained in Example A-1 (4) and (+)-trans-3-(N-t-butoxycarbonylmethylamino)-4-methoxypyrrolidine obtained in Example B-2, there was produced (−)-7-[trans-3-(N-t-butoxycarbonylmethylamino)-4-methoxy-1-pyrrolidinyl]-1,4-dihydro-4-oxo-1-(2-thiazolyl)-1,8-naphthyridine-3-carboxylic acid ethyl ester (amorphous) in the same manner as in Example C-1 (1).

[a]$_D^{29}$−9.1° (c=1.006, chloroform)

(2) The above-captioned hydrochloride (Compound 1-2) was obtained from the ethyl ester obtained in the above (1), according to the process described in Example C-1 (2).

Melting point: 278°–282° C. (decomposed)

[a]$_D^{29}$+24.8° (c=0.500, water)

(3) A solution composed of the hydrochloride (28.1 g) obtained in the above (2), water (300 ml) and aqueous ammonia (25 ml) was stirred overnight at 50° C., and was then concentrated under reduced pressure. Crystals were washed with water and methanol to give the desired carboxylic acid (Compound 1-2-1) (19.5 g).

Melting point: 268°–271° C.

[a]$_D^{30}$+53.1° (c=1.005, 1N NaOH)

Example C-3 Preparation of desired compound (I) (−)-1,4-Dihydro-7-(trans-3-methoxy-4-methylamino-1-pyrrolidinyl)-4-oxo-1-(2-thiazolyl)- 1,8-naphthyridine-3-carboxylic acid hydrochloride (Compound 1–3)

(1) With use of 7-chloro-1,4-dihydro-4-oxo-1-(2-thiazolyl)-1,8-naphthyridine-3-carboxylic acid ethyl ester obtained in Example A-1 (4) and (−)-trans-3-(N-t-butoxycarbonylmethylamino)-4-methoxypyrrolidine obtained in Example B-3, there was obtained (+)-7-[trans-3-(N-t-butoxycarbonylmethylamino)-4-methoxy-1-pyrrolidinyl]-1,4-dihydro-4-oxo-1-(2-thiazolyl)-1,8-naphthyridine-3-carboxylic acid ethyl ester (amorphous) in the same manner as in Example C-1 (1).

[a]$_D^{29}$+9.0° (c=1.002, chloroform)

(2) The above-captioned compound was obtained from the ethyl ester produced in the above (1), according to the procedure described in Example C-1 (2).

Melting point: 278°–282° C. (decomposed)

[a]$_D^{29}$−25.2° (c=0.504, water)

Examples C-4 and C-5 Preparation of desired compound (I)

The following compounds were obtained according to almost the same procedure as described in Example C-1.

| Example | Compound No. | Y' | Ra | X | Melting point (°C.) |
|---|---|---|---|---|---|
| C-4 | | CH$_3$NH, CH$_3$O (pyrrolidinyl) | Et* | — | 253–259 (decomposed) |
| | 1–4 | Same as above | H | HCl | 263–269 (decomposed) |
| C-5 | | H$_2$N, CH$_3$O''' (pyrrolidinyl) | Et | — | 98–100 |
| | 2 | Same as above | H | HCl | 268–271 (decomposed) |

*Et denotes ethyl. (the same applies in the followings)

Example C-6 Preparation of desired product (I) 7-(3-Amino-1-pyrrolidinyl)-1,4-dihydro-4-oxo-1-(2-thiazolyl)-1,8-naphthyridine-3-carboxylic acid hydrochloride (Compound 3) and its L-Ala derivative (Compound 3-1)

(1) Acetonitrile (10 ml) containing 3-aminopyrrolidine (1.6 g) was added dropwise to a suspension composed of the ester (2.0 g) obtained in Example A-1 (4) and acetonitrile (80 ml). The resulting mixture was stirred at room temperature for one hour and a half, and crystal was taken by filtration. Thus, 7-(3-amino-1-pyrrolidinyl)-1,4-dihydro-4-oxo-1-(2-thiazolyl)-1,8-naphthyridine-3-carboxylic acid ethyl ester (1.89 g) was produced by recrystallization from a mixed solution composed of chloroform, methanol and diisopropylether.

Melting point: 219°–221° C.

(2) A suspension composed of the above ester (1.0 g) and a 10% aqueous solution of hydrochloric acid (15 ml) was stirred at 95° C. for 3.5 hours. Crystals were taken by filtration, and washed with a mixed solution composed of chloroform and methanol to give 7-(3-amino-1-pyrrolidinyl)-1,4-dihydro-4-oxo-1-(2-thiazolyl)-1,8-naphthyridine-3-carboxylic acid hydrochloride (Compound 3)(0.93 g).

Melting point: 267° C. (decomposed)

(3) To a mixture composed of the ethylester (2.1 g) obtained in the above (1), N-t-butoxycarbonyl-L-alanine (1.5 g) and methylene chloride (80 ml), there was added 1.6 g of 1-ethyl-3-(3-dimethylaminopropyl)carbodiimide hydrochloride (WSC), and the resulting mixture was stirred at room temperature for two hours. After washed with an aqueous solution of sodium hydrogen carbonate, the mixture was dried over anhydrous sodium sulfate, and was then concentrated under reduced pressure, and was subsequently purified by silica gel column chromatography (eluent chloroform:methanol=20:1) to give 7-[3-(N-t-butoxycarbonyl-L-alanyl)amino-1-pyrrolidinyl]-1,4-dihydro-4-oxo-1-(2-thiazolyl)-1,8-naphthyridine-3-carboxylic acid ethyl ester (2.9 g).

Melting point: 138°–140° C.
[a]$_D^{27}$ –46° (c=1.0, chloroform)

(4) A mixture composed of the ester (1.4 g) obtained in the above (3), 0.5N hydrochloric acid (30 ml) and ethanol (16 ml) was stirred at 70° C. for two days. Solvent was concentrated under reduced pressure, and 7-(3-L-alanylamino-1-pyrrolidinyl)-1,4-dihydro-4-oxo-1-(2-thiazolyl)-1,8-naphthyridine-3-carboxylic acid hydrochloride (Compound 3-1) (0.77 g) was obtained by recrystallization from 10% hydrochloric acid and ethanol.

Melting point: 229°–231° C. (decomposed)
[a]$_D^{27}$ +10° (c=0.5, water)

Examples C-7–C-10 Preparation of desired product (I)
The following compounds were produced by almost the same method as mentioned in Example C-1.

| Example | Compound No. | Y' | Ra | X | Melting point (°C.) |
|---|---|---|---|---|---|
| C-7 | | CH$_3$–N(Boc)–C(CH$_3$)– pyrrolidinyl | Et | — | 95–97 |
| | 4 | CH$_3$NH–C(CH$_3$)– pyrrolidinyl | H | HCl | 297–299 (decomposed) |
| C-8 | | CH$_3$–N(Boc)– (CH$_3$···) pyrrolidinyl | Et | — | 154–156 |
| | 5 | CH$_3$NH– (CH$_3$···) pyrrolidinyl | H | HCl | 279–282 (decomposed) |
| C-9 | | CH$_3$NH–pyrrolidinyl | Et | — | 157–159 |
| | 6 | Same as the above | H | HCl | 266–270 (decomposed) |
| C-10 | | BocNH– (CH$_3$···) pyrrolidinyl | Et | — | 238–240 |
| | 7 | H$_2$N– (CH$_3$···) pyrrolidinyl | H | HCl | 269–271 (decomposed) |

*Boc denotes t-butoxycarbonyl. (the same applies in the followings)

Example C-11 Preparation of desired product (I) 7-(3-Amino-1-pyrrolidinyl)-1-(4-fluoro-2-thiazolyl)-1,4-dihydro-4-oxo-1,8-naphthyridine-3-carboxylic acid hydrochloride (Compound 8)

(1) A mixture composed of 7-chloro-1-(4-fluoro-2-thiazoly)-1,4-dihydro-4-oxo-1,8-naphthyridine-3-carboxylic acid ethyl ester (30 mg) obtained in Example A-2, 3-(t-butoxycarbonylamino)pyrrolidine (19 mg), triethylamine (26 mg) and acetonitrile (10 ml) was stirred at room temperature for 30 minutes. Solvent was distilled off under reduced pressure, and water was added, and then, the resulting mixture was extracted with chloroform. The obtained extract was dried over anhydrous sodium sulfate, and solvent was distilled off under reduced pressure. The resulting residue was subjected to recrystallization with use of ethyl acetate, and thus, there was obtained 7-(3-t-butoxycarbonylamino-1-pyrrolidinyl)-1-(4-fluoro-2-thiazolyl)-1,4-dihydro-4-oxo-1,8-naphthyridine-3-carboxylic acid ethyl ester (40 mg).

Melting point: 233°–234° C.

(2) A solution composed of the above ester (40 mg) and 20% hydrochloric acid (2 ml) was heated to reflux for 1.5 hour. After cooling, crystal was taken by filtration, and was then washed with dilute aqueous solution of hydrochloric acid, and thus, the above-captioned Compound 8 (32 mg) was obtained.

Melting point: 283°–284° C. (decomposed)

Example C-12 Preparation of desired product (I) 5-Amino-7-(3-amino-1-pyrrolidinyl)-1,4-dihydro-4-oxo-1-(2-thiazolyl)-1,8-naphthyridine-3-carboxylic acid hydrochloride (Compound 9)

(1) 5-Amino-7-chloro-1,4-dihydro-4-oxo-1-(2-thiazolyl)-1,8-naphthyridine-3-carboxylic acid (1.0 g) obtained in Example A-4 (2) and aminopyrrolidine (800 mg) were made to react in almost the same manner as in Example C-1, and thus, the above-captioned Compound 9 (610 mg) was produced.

Melting point: 261°–263° C.

Examples C-13 Preparation of desired product (I)
The following compounds were produced by almost the same method as mentioned in Example C-1.

| Example | Compound No. | Y' | Ra | X | Melting point (°C.) |
|---|---|---|---|---|---|
| C-13 | | H$_2$N–C(CH$_3$)– pyrrolidinyl | Et | — | 248–251 |
| | 10 | Same as the above | H | HCl | 243–246 |

Example C-14 Preparation of desired product (I) 3-Formyl-1,4-dihydro-7-(trans-3-methoxy-4-methylamino-1-pyrrolidinyl)-4-oxo-1-(2-thiazolyl)-1,8-naphthyridine hydrochloride (Compound 11)

(1) Triethylamine (13.4 ml) was added to a suspension composed of 7-chloro-1,4-dihydro-4-oxo-1-(2-thiazolyl)-1,8-naphthyridine-3-carboxylic acid ethyl ester (8.49 g) obtained in Example A-1 (4), trans-3-methoxy-4-methylaminopyrrolidine dihydrochloride (6.5 g) and acetonitrile (400 ml). After stirred overnight at room temperature, the resulting reaction mixture was concentrated under reduced pressure. Then, an aqueous solution of sodium hydrogen carbonate was added, and the resultant mixture was extracted with chloroform. The obtained extract was washed with saturated brine, and was then dried over anhydrous sodium sulfate, and thereafter, solvent was distilled off under reduced pressure. Methylene chloride (500 ml) was added to the obtained residue, and, to the resultant mixture, di-t-butyl dicarbonate (6.4 g) was added under ice cooing. After stirred overnight at room temperature, the resulting reaction mixture was concentrated under reduced pressure, and the resultant residue was purified by silica gel column chromatography (eluent chloroform:methanol=100:1) to give 7-[trans-3-(N-t-butoxycarbonylmethylamino)-4-methoxy-1-pyrrolidinyl]-1,4-dihydro-4-oxo-1-(2-thiazolyl)-1,8-naphthyridine-3-carboxylic acid ethyl ester (9.1 g).

IR (KBr) cm$^{-1}$: 1735, 1695

MS (m/z): 530 (MH$^+$)

(2) A 1N aqueous solution of sodium hydroxide (150 ml) was added to a mixture composed of the compound (8.95 g) obtained in the above (1) and ethanol (150 ml), and the resulting mixture was stirred at the same temperature for 30 minutes, and overnight at room temperature. Then, the mixture was made acidic with an aqueous solution of acetic acid, and was then extracted with chloroform. The obtained extract was washed with saturated brine, and was then dried over anhydrous sodium sulfate. Solvent was distilled off under reduced pressure, and thus, 7-[trans-3-(N-t-butoxycarbonylmethylamino)-4-methoxy-1-pyrrolidinyl]-1,4-dihydro- 4-oxo-1-(2-thiazolyl)-1,8-naphthyridine-3-carboxylic acid (7.19 g) was obtained.

Melting point: 185°–188° C.

IR (KBr) cm$^{-1}$: 1715, 1690

MS (m/z): 502 (MH$^+$)

(3) To a mixture composed of the compound (7.15 g) obtained in the above (2) and methanol (400 ml), there was added 2.16 g of sodium borohydride under ice cooling, and the resulting mixture was stirred for 15 minutes at the same temperature and then stirred overnight at room temperature. Solvent was distilled off under reduced pressure, and the obtained residue was extracted with chloroform. The resultant extract was washed with saturated brine, and was then dried over anhydrous sodium sulfate. Solvent was distilled off under reduced pressure, and the obtained residue was subsequently purified by silica gel column chromatography (eluent chloroform:methanol=100:1) to give 7-[trans-3-(N-t-butoxycarbonylmethylamino)-4-methoxy-1-pyrrolidinyl]-1,2,3,4-tetrahydro-4-oxo-1-(2-thiazolyl)-1,8-naphthyridine (3.9 g).

IR (neat) cm$^{-1}$: 1690

MS (m/z): 460 (MH$^+$)

(4) The compound (3.8 g) obtained in the above (3) was dissolved in tetrahydro furan (500 ml), and, to the resulting solution, there was added dropwise 6.1 ml of a solution of n-butylithium (1.6M) in n-hexane at a temperature of −78° C. After the obtained solution was stirred for 30 minutes at the same temperature, ethyl formate (1.34 ml) was added, and then, temperature was raised slowly, and the resultant mixture was stirred overnight. Solvent was distilled off under reduced pressure, and an aqueous solution of acetic acid was added to the obtained residue, and then, the resulting mixture was extracted with chloroform. The resultant extract was washed with saturated brine, and was then dried over anhydrous sodium sulfate. Solvent was distilled off under reduced pressure, and thus, 7-[trans-3-(N-t-butoxycarbonylmethylamino)-4-methoxy-1-pyrrolidinyl]-3-formyl-1,2,3,4-tetrahydro-4-oxo-1-(2-thiazolyl)-1,8-naphthyridine (3.87 g) was obtained.

IR (neat) cm$^{-1}$: 1690, 1615

MS (m/z): 488 (MH$^+$)

(5) The compound (3.6 g) obtained in the above (4) was dissolved in 1,4-dioxane (160 ml), and, to the resulting solution, 2,3-dichloro-5,6-dicyanobenzo-quinone (2.51 g) was gradually added. After the resultant mixture was stirred for 2.5 hours, solvent was distilled off under reduced pressure, and an aqueous solution of sodium hydroxide was added to the obtained residue, and the resultant mixture was extracted with chloroform. The resultant extract was washed with saturated brine, and was then dried over anhydrous sodium sulfate. Solvent was distilled off under reduced pressure, and the obtained residue was subsequently purified by silica gel column chromatography (eluent chloroform:methanol=100:1) to give 7- [trans-3-(N-t-butoxycarbonylmethylamino)-4-methoxy-1-pyrrolidinyl]-3-formyl-1,4-dihydro-4-oxo-1-(2-thiazolyl)-1,8-naphthyridine (1.73 g).

Melting point: 130°–132° C.

IR (KBr) cm$^{-1}$: 1695, 1645, 1615

MS (m/z): 486 (MH$^+$)

(6) A mixture composed of the compound (1.65 g) obtained in the above (5), a 10% aqueous solution of hydrochloric acid and ethanol (40 ml) was heated at 50°–60° C. for seven hours. Crystal was taken by filtration, and was then washed with ethanol and diisopropylether to give 3-formyl-1,4-dihydro-7-(trans-3-methoxy-4-methylamino-1-pyrrolidinyl)-4-oxo-1-(2-thiazolyl)-1,8-naphthyridine hydrochloride (Compound 11) (1.05 g).

Melting point: 255°–263° C. (decomposed)

IR (KBr) cm$^{-1}$: 3460, 1695, 1645

MS (m/z): 386 (MH$^+$)

Examples C-5–C-27 Preparation of desired product (I)

The following compounds were produced according to the method mentioned in Example C-1.

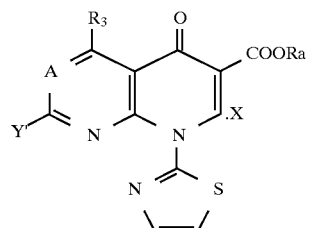

| Example | Compound No. | A | $R_s$ | $R_1$ | Y' | Ra | X | Melting point (°C.) |
|---|---|---|---|---|---|---|---|---|
| C-15 | | CH | H | H | H₂N-[3,4-dimethylpyrrolidinyl] | Et | — | 92–95 |
| | 12 | CH | H | H | Same as the above | H | HCl | 245–248 |
| C-16 | | CH | H | H | C₂H₅NH-[4-methoxypyrrolidinyl] | Et | — | amorphous |
| | 13 | CH | H | H | Same as the above | H | HCl | 293–295 (decomposed) |
| C-17 | | N | H | H | H₂N-[3-pyrrolidinyl] | Et | — | 228–230 |
| | 14 | N | H | H | Same as the above | H | HCl | 288–291 (decomposed) |
| C-18 | 15 | CH | NH₂ | H | CH₃NH-[4-methoxypyrrolidinyl] | H | — | 247–250 |
| C-19 | | CH | H | F | CH₃NH-[4-methoxypyrrolidinyl] | Et | — | 198–199 |
| | 16 | CH | H | F | Same as the above | H | HCl | 277–279 (decomposed) |

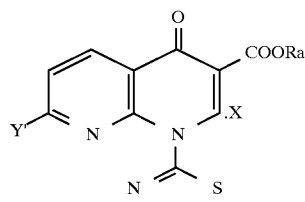

| Example | Compound No. | $R_1$ | $R_1'$ | Y' | Ra | X | Melting point (°C.) |
|---|---|---|---|---|---|---|---|
| C-20 | | H | H | AcNH-[2-methyl-3-pyrrolidinyl] | Et | — | 152–155 |
| | 17 | H | H | H₂N-[2-methyl-3-pyrrolidinyl] | H | HCl | 296–299 (decomposed) |

-continued

| Example | Compound No. | R₁ | R₃ | Y' | | Ra | X | Melting point (°C.) |
|---|---|---|---|---|---|---|---|---|
| C-21 | | F | H | H₂N–[pyrrolidine-CH₃] | | Et | — | 246–247 |
| | 18 | F | H | Same as the above | | H | HCl | 300 or higher |
| C-22 | | H | Cl | BocNH–[pyrrolidine] | | Et | — | 228–229 |
| | 19 | H | Cl | H₂N–[pyrrolidine] | | H | HCl | 236–237 |
| C-23 | | H | H | BocNH–[pyrrolidine-CH₃] | | Et | — | 236–238 |
| | 20 | H | H | H₂N–[pyrrolidine-CH₃] | | H | HCl | 259–262 (decomposed) |

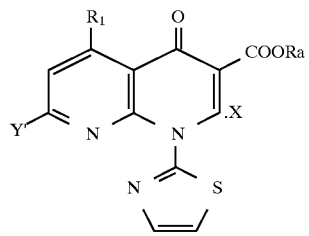

| Example | Compound No. | R₃ | Y' | Ra | X | Melting point (°C.) |
|---|---|---|---|---|---|---|
| C-24 | | H | C₂H₅–N(Boc)–CH₂–[pyrrolidine] | Et | — | 109–111 |
| | 21 | H | C₂H₅NH–CH₂–[pyrrolidine] | H | HCl | 300 or higher |
| C-25 | | CF₃ | H₂N–[pyrrolidine] | Et | — | 208–209 |
| | 22 | CF₃ | Same as the above | H | HCl | 291–292 (decomposed) |
| C-26 | 23 | Cl | H₂N–[pyrrolidine] | H | HCl | 300 or higher |
| C-27 | | H | BocNH–[Cl-pyrrolidine] | Et | — | 128–132 |

| 24 | H | H₂N group on pyrrolidine | H | HCl | 285–288 (decomposed) |

*Ac: acetyl

Example C-28 Preparation of desired product (I) 1,4-Dihydro-7-(trans-3-methylamino-4-methylthio-1-pyrrolidinyl)-4-oxo-1-(2-thiazolyl)-1,8-naphthyridine-3-carboxylic acid hydrochloride (Compound 25)

(1) With use of 7-chloro-1,4-dihydro-4-oxo-1-(2-thiazolyl)-1,8-naphthyridine-3-carboxylic acid ethyl ester obtained in Example A-1 (4) and trans-3-methylamino-4-methylthiopyrrolidine, there was obtained 1,4-dihydro-7-(trans-3-methylamino-4-methylthio-1-pyrrolidinyl)-4-oxo-1-(2-thiazolyl)-1,8-naphthyridine-3-carboxylic acid ethyl ester in the same manner as in Example C-1 (1).

Melting point: 164°–165° C.

(2) The above-captioned compound was produced from the ethyl ester obtained in the above (1), in accordance with the process mentioned in Example C-1 (2).

Melting point: 271°–272° C.

4. Series D

Example D-1 Preparation of liquid agent
Prescription

| Compound 1-1 | 2 g |
| Sorbitol | 50 g |
| Sodium hydroxide | appropriate amount |
| Distilled water for injection | appropriate amount 1000 ml |

Preparation method:

Compound 1-1 and sorbitol were dissolved in part of distilled water for injection, and the residual distilled water was added so that pH of the resultant solution might be adjusted to be 4.0. This solution was filtered with a membrane filter (0.22 μm) to give a liquid for injection.

Example D-2 Preparation of freeze-dried agent
Prescription

| Compound 1-1 | 1 g |
| Mannitol | 5 g |
| Sodium hydroxide | appropriate amount |
| Distilled water for injection | appropriate amount 100 ml |

Preparation method

Compound 1-1 and mannitol were dissolved in part of distilled water for injection, and the residual distilled water was added so that pH of the resultant solution might be adjusted to be 5.0. This solution was filtered with a membrane filter (0.22 μm), and the obtained filtrate was freeze-dried to give a powder agent for injection.

Industrial Applicability

The compound of this invention is useful as medicine, in particular as anti-tumor agent, for mammals including human beings.

We claim:

1. A pyridone-carboxylic acid derivative having the following general formula (I), or a salt thereof:

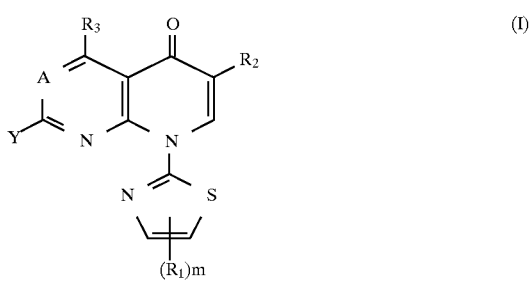

wherein
$R_1$ is a hydrogen atom, a lower alkoxy group, a halogen atom, a lower alkyl group which may be substituted with halogen atom, or a phenyl group which may be substituted with halogen atom;

$R_2$ is a carboxyl group or a group convertible to a carboxyl group;

$R_3$ is a hydrogen atom, an amino group which may be protected, a halogen atom or a lower alkyl group which may be substituted with halogen atom;

A is CH;

m is an integer of 1 or 2; and

Y is an eliminatable group selected from the group consisting of a halogen atom, a lower alkoxy group, a lower alkylthio group, a lower alkylsulfinyl group, a lower alkylsulfonyl group, an arylsulfonyl group, a lower alkylsulfonyloxy group and an arylsulfonyloxy group, or a group having the following formula Y'

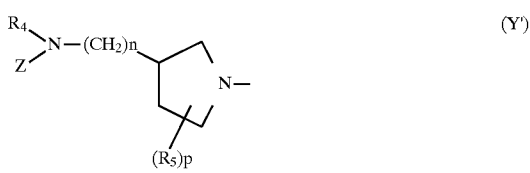

wherein $R_4$ is a hydrogen atom or a lower alkyl group;

Z is a hydrogen atom, a lower alkyl group or a Z group convertible to a hydrogen atom;

$R_5$ is a hydrogen atom, a halogen atom, a lower alkoxy group, a lower alkylthio group or a lower alkyl group which may be substituted with halogen atom;

n is an integer of 0 or 1; and p is an integer of 1, 2, 3 or 4.

2. A pyridone-carboxylic acid derivative or salt thereof of claim 1 wherein Y is an eliminatable group in the above formula (I).

3. A pyridone-carboxylic acid derivative having the following formula (I-a) or salts thereof:

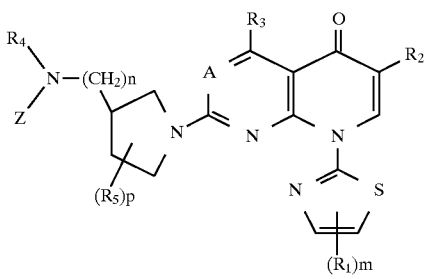

wherein
$R_1$ is a hydrogen atom, a lower alkoxy group, a halogen atom, a lower alkyl group which may be substituted with halogen atom, or a phenyl group which may be substituted with halogen atom;
$R_2$ is a carboxyl group or a group convertible to a carboxyl group;
$R_3$ is a hydrogen atom, an amino group which may be protected, a halogen atom or a lower alkyl group which may be substituted with halogen atom;
$R_4$ is a hydrogen atom or a lower alkyl group;
Z is a hydrogen atom, a lower alkyl group or a group convertible to a hydrogen atom;
$R_5$ is a hydrogen atom, a halogen atom, a lower alkoxy group, a lower alkylthio group or a lower alkyl group which may be substituted with halogen atom;
A is CH;
m is an integer of 1 or 2;
n is an integer of 0 or 1; and
p is an integer of 1, 2, 3 or 4.

4. A pyridone-carboxylic acid derivative of claim 3 whose salts are either salts derived from the carboxyl group of $R_2$ of formula (I-a) or acid addition salts derived from the basic substituent group portion which is bound to the 3-position of the 1-pyrrolidinyl group.

5. A pyridone-carboxylic acid derivative or salt thereof of claim 3 wherein the group convertible to a carboxyl group in $R_2$ of formula (I-a) is a formyl group or an ester.

6. A pyridone-carboxylic acid derivative or salt thereof of claim 3 wherein the group convertible to a hydrogen atom in Z of formula (I-a) is an amino acid residue or a peptide residue.

7. A pyridone-carboxylic acid derivative having the following formula (I-b) or salt thereof:

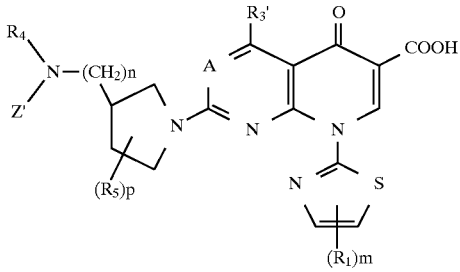

wherein
$R_1$ is a hydrogen atom, a lower alkoxy group, a halogen atom, a lower alkyl group which may be substituted with halogen atom, or a phenyl group which may be substituted with halogen atom;
$R_3'$ is a hydrogen atom, amino group, halogen atom or lower alkyl group which may be substituted with halogen atom;

$R_4$ is a hydrogen atom or a lower alkyl group;
Z' is a hydrogen atom or a lower alkyl group;
$R_5$ is a hydrogen atom, a halogen atom, a lower alkoxy group, a lower alkylthio group or a lower alkyl group which may be substituted with halogen atom;
A is CH;
m is an integer of 1 or 2;
n is an integer of 0 or 1; and
p is an integer of 1, 2, 3 or 4.

8. A pyridone-carboxylic acid derivative or salt thereof of claim 7 wherein both m and p are 1, and n is 0 in formula (I-b).

9. A pyridone-carboxylic acid derivative or salt thereof of claim 7 wherein A is CH, both m and p are 1, n is 0, $R_1$ is a hydrogen atom or a fluorine atom, $R_3'$ is a hydrogen atom, $R_4$ is a hydrogen atom or a lower alkyl group, Z' is a hydrogen atom, $R_5$ is a lower alkyl group or a lower alkoxy group in formula (I-b).

10. A pyridone-carboxylic acid derivative of claim 1 or 3 which is 1,4-dihydro-7-(3-methoxy-4-methylamino-1-pyrrolidinyl)-4-oxo-1-(2-thiazolyl)-1,8-naphthyridine-3-carboxylic acid or a salt thereof.

11. A pyridone-carboxylic acid derivative of claim 10 which is either cis isomer or trans isomer of 1,4-dihydro-7-(3-methoxy-4-methylamino-1-pyrrolidinyl)-4-oxo-1-(2-thiazolyl)-1,8-naphthyridine-3-carboxylic acid, or an optically active substance thereof, or a salt thereof.

12. An anti-tumor agent which contains, as an effective ingredient, either a pyridone-carboxylic acid derivative of formula (I-a) of claim 3 a physiologically acceptable salt thereof.

13. An anti-tumor agent which contains, as an effective ingredient, either the pyridone-carboxylic acid derivative of formula (I-b) of claim 7 or a physiologically acceptable salt thereof.

14. The anti-tumor agent of claim 12 or 13 which is an agent for the treatment or prophylaxis of non-solid tumor or solid tumor.

15. The anti-tumor agent of claim 14 wherein said non-solid tumor is leukemia or malignant lymphoma.

16. The anti-tumor agent of claim 14 wherein said solid tumor is one which occurs in tissues of lung, breast, stomach, skin, ovary, uterus, intestine, urinary bladder, nasopharynx, head and neck, esophagus, liver, biliary tract, pancreas, kidney, testis, prostate, bone or brain.

17. A pharmacological composition which comprises a pyridone-carboxylic acid derivative of formula (I-a) of claim 3 or of formula (I-b) of claim 7 or physiologically acceptable salt thereof, and a pharmacologically acceptable carrier.

18. The composition of claim 17 wherein said carrier is a solvent.

19. The pharmacological composition of claim 17 which is in the form of a solution.

20. The pharmacological composition of claim 19 which is an agent for injection or transfusion.

21. The pharmacological composition of claim 17 which is a freeze-dried preparation.

* * * * *